United States Patent
Aizenfeld et al.

(10) Patent No.: US 10,634,900 B2
(45) Date of Patent: Apr. 28, 2020

(54) SYSTEMS AND METHODS FOR IMAGE MAGNIFICATION USING RELATIVE MOVEMENT BETWEEN AN IMAGE SENSOR AND A LENS ASSEMBLY

(71) Applicant: EndoChoice, Inc., Alpharetta, GA (US)

(72) Inventors: Amram Aizenfeld, Ramot Menashe (IL); Leonid Krivopisk, Nesher (IL)

(73) Assignee: EndoChoice, Inc., Alpharetta, GA (US)

( * ) Notice: Subject to any disclaimer, the term of this patent is extended or adjusted under 35 U.S.C. 154(b) by 0 days.

(21) Appl. No.: 16/107,573

(22) Filed: Aug. 21, 2018

(65) Prior Publication Data

US 2019/0004306 A1    Jan. 3, 2019

Related U.S. Application Data

(63) Continuation of application No. 15/074,807, filed on Mar. 18, 2016, now Pat. No. 10,078,207.

(60) Provisional application No. 62/134,742, filed on Mar. 18, 2015.

(51) Int. Cl.
| | |
|---|---|
| *G02B 23/24* | (2006.01) |
| *H04N 5/232* | (2006.01) |
| *A61B 1/00* | (2006.01) |
| *H04N 5/225* | (2006.01) |
| *A61B 1/05* | (2006.01) |

(52) U.S. Cl.
CPC ...... *G02B 23/2438* (2013.01); *A61B 1/00096* (2013.01); *A61B 1/00188* (2013.01); *A61B 1/051* (2013.01); *G02B 23/2484* (2013.01); *H04N 5/2252* (2013.01); *H04N 5/2253* (2013.01); *H04N 5/2254* (2013.01); *H04N 5/23296* (2013.01); *H04N 2005/2255* (2013.01)

(58) Field of Classification Search
None
See application file for complete search history.

(56) References Cited

U.S. PATENT DOCUMENTS

| | | |
|---|---|---|
| 3,639,714 A | 2/1972 | Fujimoto |
| 3,955,064 A | 5/1976 | Demetrio |
| 4,027,697 A | 6/1977 | Bonney |
| (Continued) | | |

FOREIGN PATENT DOCUMENTS

| | | |
|---|---|---|
| CA | 2297986 | 3/1999 |
| CA | 2765559 | 12/2010 |
| (Continued) | | |

OTHER PUBLICATIONS

Office Action dated Jun. 30, 2016 for U.S. Appl. No. 13/655,120.
(Continued)

*Primary Examiner* — Kate H Luo
(74) *Attorney, Agent, or Firm* — Bookoff McAndrews, PLLC

(57) ABSTRACT

The present specification describes a novel system for dynamically modifying the magnification power of optical devices used in high performance and critical applications such as medical procedures. The present specification describes an optical imaging system having a magnification control system connected to a sensor device for enabling movement of sensor device with respect to a lens assembly of the imaging system, wherein distance between the sensor device and the lens assembly is altered to enable different levels of magnification capability.

14 Claims, 13 Drawing Sheets

(56) References Cited

U.S. PATENT DOCUMENTS

| | | | |
|---|---|---|---|
| 4,037,588 A | 7/1977 | Heckele | |
| 4,084,401 A | 4/1978 | Belardi | |
| 4,402,313 A | 9/1983 | Yabe | |
| 4,461,282 A | 7/1984 | Ouchi | |
| 4,494,549 A | 1/1985 | Namba | |
| 4,532,918 A | 8/1985 | Wheeler | |
| 4,588,294 A | 5/1986 | Siegmund | |
| 4,641,635 A | 2/1987 | Yabe | |
| 4,727,859 A | 3/1988 | Lia | |
| 4,764,001 A | 8/1988 | Yokota | |
| 4,801,792 A | 1/1989 | Yamasita | |
| 4,825,850 A | 5/1989 | Opie | |
| 4,877,314 A | 10/1989 | Kanamori | |
| 4,902,115 A | 2/1990 | Takahashi | |
| 4,976,522 A | 12/1990 | Igarashi | |
| 4,984,878 A | 1/1991 | Miyano | |
| 5,007,406 A | 4/1991 | Takahashi | |
| 5,014,685 A | 5/1991 | Takahashi | |
| 5,193,525 A | 3/1993 | Silverstein | |
| 5,224,929 A | 7/1993 | Remiszewski | |
| 5,296,971 A | 3/1994 | Mori | |
| 5,359,456 A | 10/1994 | Kikuchi | |
| 5,395,329 A | 3/1995 | Fleischhacker | |
| 5,447,148 A | 9/1995 | Oneda | |
| 5,460,167 A | 10/1995 | Yabe | |
| 5,464,007 A | 11/1995 | Krauter | |
| 5,475,420 A | 12/1995 | Buchin | |
| 5,489,256 A | 2/1996 | Adair | |
| 5,518,501 A | 5/1996 | Oneda | |
| 5,518,502 A | 5/1996 | Kaplan | |
| 5,547,455 A | 8/1996 | McKenna | |
| 5,547,457 A | 8/1996 | Tsuyuki | |
| 5,575,755 A | 11/1996 | Krauter | |
| 5,587,839 A | 12/1996 | Miyano | |
| 5,630,782 A | 5/1997 | Adair | |
| 5,630,798 A | 5/1997 | Beiser | |
| 5,662,588 A | 9/1997 | Iida | |
| 5,674,182 A | 10/1997 | Suzuki | |
| 5,674,205 A * | 10/1997 | Pasricha | A61K 38/4893 222/327 |
| 5,685,821 A | 11/1997 | Pike | |
| 5,685,823 A | 11/1997 | Ito | |
| 5,702,347 A | 12/1997 | Yabe | |
| 5,707,344 A | 1/1998 | Nakazawa | |
| 5,725,474 A | 3/1998 | Yasui | |
| 5,725,476 A | 3/1998 | Yasui | |
| 5,725,477 A | 3/1998 | Yasui | |
| 5,725,478 A | 3/1998 | Saad | |
| 5,754,313 A * | 5/1998 | Pelchy | A61B 1/042 348/65 |
| 5,777,797 A | 7/1998 | Miyano | |
| 5,782,751 A | 7/1998 | Matsuno | |
| 5,800,341 A | 9/1998 | McKenna | |
| 5,810,715 A | 9/1998 | Moriyama | |
| 5,810,717 A | 9/1998 | Maeda | |
| 5,810,770 A | 9/1998 | Chin | |
| 5,830,121 A | 11/1998 | Enomoto | |
| 5,836,894 A | 11/1998 | Sarvazyan | |
| 5,860,913 A | 1/1999 | Yamaya | |
| 5,870,234 A | 2/1999 | EbbesmeierneeSchitthof | |
| 5,916,148 A | 6/1999 | Tsuyuki | |
| 5,940,126 A | 8/1999 | Kimura | |
| 6,058,109 A | 5/2000 | Lechleider | |
| 6,095,970 A | 8/2000 | Hidaka | |
| 6,095,971 A | 8/2000 | Takahashi | |
| 6,117,068 A | 9/2000 | Gourley | |
| 6,181,481 B1 | 1/2001 | Yamamoto | |
| 6,196,967 B1 * | 3/2001 | Lim | A61B 1/00128 600/125 |
| 6,261,226 B1 | 7/2001 | McKenna | |
| 6,277,064 B1 | 8/2001 | Yoon | |
| 6,359,674 B1 | 3/2002 | Horiuchi | |
| 6,375,610 B2 | 4/2002 | Verschuur | |
| 6,402,738 B1 | 6/2002 | Ouchi | |
| 6,419,626 B1 | 7/2002 | Yoon | |
| 6,476,851 B1 | 11/2002 | Nakamura | |
| 6,520,908 B1 | 2/2003 | Ikeda | |
| 6,636,254 B1 | 10/2003 | Onishi | |
| 6,638,214 B2 | 10/2003 | Akiba | |
| 6,673,011 B1 * | 1/2004 | Hilger | G01M 11/0221 305/117 |
| 6,673,012 B2 | 1/2004 | Fujii | |
| 6,690,337 B1 | 2/2004 | Mayer, III | |
| 6,712,760 B2 | 3/2004 | Sano | |
| 6,832,984 B2 | 12/2004 | Stelzer | |
| 6,888,119 B2 | 5/2005 | Iizuka | |
| 6,997,871 B2 | 2/2006 | Sonnenschein | |
| 7,154,378 B1 | 12/2006 | Ertas | |
| 7,435,218 B2 | 10/2008 | Krattiger | |
| 7,621,869 B2 | 11/2009 | Ratnakar | |
| 7,630,148 B1 | 12/2009 | Yang | |
| 7,701,650 B2 | 4/2010 | Lin | |
| 7,713,246 B2 | 5/2010 | Shia | |
| 7,746,572 B2 | 6/2010 | Asami | |
| 7,813,047 B2 | 10/2010 | Wang | |
| 7,828,725 B2 | 11/2010 | Maruyama | |
| 7,918,788 B2 | 4/2011 | Lin | |
| 7,927,272 B2 | 4/2011 | Bayer | |
| 7,967,745 B2 | 6/2011 | Gilad | |
| 7,976,462 B2 | 7/2011 | Wright | |
| 8,064,666 B2 | 11/2011 | Bayer | |
| 8,182,422 B2 | 5/2012 | Bayer | |
| 8,197,399 B2 | 6/2012 | Bayer | |
| 8,235,887 B2 | 8/2012 | Bayer | |
| 8,262,558 B2 | 9/2012 | Sato | |
| 8,287,446 B2 | 10/2012 | Bayer | |
| 8,289,381 B2 | 10/2012 | Bayer | |
| 8,300,325 B2 | 10/2012 | Katahira | |
| 8,310,530 B2 | 11/2012 | Bayer | |
| 8,353,860 B2 | 1/2013 | Boulais | |
| 8,447,132 B1 | 5/2013 | Galil | |
| 8,449,457 B2 | 5/2013 | Aizenfeld | |
| 8,460,182 B2 | 6/2013 | Ouyang | |
| 8,585,584 B2 | 11/2013 | Ratnakar | |
| 8,587,645 B2 | 11/2013 | Bayer | |
| 8,672,836 B2 | 3/2014 | Higgins | |
| 8,715,168 B2 | 5/2014 | Ratnakar | |
| 8,797,392 B2 | 8/2014 | Bayer | |
| 8,872,906 B2 | 10/2014 | Bayer | |
| 8,926,502 B2 | 1/2015 | Levy | |
| 9,044,185 B2 | 6/2015 | Bayer | |
| 9,101,266 B2 | 8/2015 | Levi | |
| 9,101,268 B2 | 8/2015 | Levy | |
| 9,101,287 B2 | 8/2015 | Levy | |
| 9,144,664 B2 | 9/2015 | Jacobsen | |
| 9,289,110 B2 | 3/2016 | Woolford | |
| 9,314,147 B2 | 4/2016 | Levy | |
| 9,320,419 B2 | 4/2016 | Kirma | |
| 2001/0036322 A1 | 11/2001 | Bloomfield | |
| 2002/0017515 A1 | 2/2002 | Obata | |
| 2002/0047897 A1 | 4/2002 | Sugimoto | |
| 2002/0087047 A1 | 7/2002 | Remijan | |
| 2002/0109771 A1 | 8/2002 | Ledbetter | |
| 2002/0109774 A1 | 8/2002 | Meron | |
| 2002/0161279 A1 | 10/2002 | Luloh | |
| 2002/0161281 A1 | 10/2002 | Jaffe | |
| 2002/0172498 A1 | 11/2002 | Esenyan | |
| 2002/0183591 A1 | 12/2002 | Matsuura | |
| 2003/0030918 A1 | 2/2003 | Murayama | |
| 2003/0063398 A1 | 4/2003 | Abe | |
| 2003/0076411 A1 | 4/2003 | Iida | |
| 2003/0083552 A1 | 5/2003 | Remijan | |
| 2003/0128893 A1 | 7/2003 | Castorina | |
| 2003/0139650 A1 | 7/2003 | Homma | |
| 2003/0153897 A1 | 8/2003 | Russo | |
| 2003/0158503 A1 | 8/2003 | Matsumoto | |
| 2003/0163029 A1 | 8/2003 | Sonnenschein | |
| 2004/0015054 A1 | 1/2004 | Hino | |
| 2004/0046865 A1 | 3/2004 | Ueno | |
| 2004/0061780 A1 | 4/2004 | Huffman | |
| 2004/0064019 A1 | 4/2004 | Chang | |
| 2004/0077927 A1 | 4/2004 | Ouchi | |
| 2004/0106850 A1 | 6/2004 | Yamaya | |
| 2004/0133072 A1 | 7/2004 | Kennedy | |

(56) References Cited

U.S. PATENT DOCUMENTS

| | | |
|---|---|---|
| 2004/0138532 A1 | 7/2004 | Glukhovsky |
| 2004/0158129 A1 | 8/2004 | Okada |
| 2004/0160682 A1 | 8/2004 | Miyano |
| 2004/0190159 A1 | 9/2004 | Hasegawa |
| 2004/0249247 A1 | 12/2004 | Iddan |
| 2004/0260151 A1 | 12/2004 | Akiba |
| 2005/0018042 A1 | 1/2005 | Rovegno |
| 2005/0020876 A1 | 1/2005 | Shioda |
| 2005/0038317 A1 | 2/2005 | Ratnakar |
| 2005/0047134 A1 | 3/2005 | Mueller |
| 2005/0057687 A1 | 3/2005 | Irani |
| 2005/0090709 A1 | 4/2005 | Okada |
| 2005/0096501 A1 | 5/2005 | Stelzer |
| 2005/0119527 A1 | 6/2005 | Banik |
| 2005/0222499 A1 | 10/2005 | Banik |
| 2005/0234296 A1 | 10/2005 | Saadat |
| 2005/0234347 A1 | 10/2005 | Yamataka |
| 2005/0251127 A1 | 11/2005 | Brosch |
| 2005/0270664 A1* | 12/2005 | Pauker .............. A61B 1/00096 359/694 |
| 2005/0272975 A1 | 12/2005 | McWeeney |
| 2005/0277808 A1 | 12/2005 | Sonnenschein |
| 2005/0283048 A1 | 12/2005 | Gill |
| 2006/0004257 A1 | 1/2006 | Gilad |
| 2006/0047184 A1 | 3/2006 | Banik |
| 2006/0063976 A1 | 3/2006 | Aizenfeld |
| 2006/0069314 A1 | 3/2006 | Farr |
| 2006/0111613 A1 | 5/2006 | Boutillette |
| 2006/0114986 A1 | 6/2006 | Knapp |
| 2006/0124358 A1 | 6/2006 | Mensa-Wilmot |
| 2006/0149129 A1 | 7/2006 | Watts |
| 2006/0171693 A1 | 8/2006 | Todd |
| 2006/0173245 A1 | 8/2006 | Todd |
| 2006/0183975 A1 | 8/2006 | Saadat |
| 2006/0184037 A1 | 8/2006 | Ince |
| 2006/0189845 A1 | 8/2006 | Maahs |
| 2006/0215406 A1 | 9/2006 | Thrailkill |
| 2006/0235306 A1 | 10/2006 | Cotter |
| 2006/0252994 A1 | 11/2006 | Ratnakar |
| 2006/0264704 A1 | 11/2006 | Fujimori |
| 2006/0293556 A1 | 12/2006 | Garner |
| 2007/0015989 A1 | 1/2007 | Desai |
| 2007/0049803 A1 | 3/2007 | Moriyama |
| 2007/0055100 A1 | 3/2007 | Kato |
| 2007/0079029 A1 | 4/2007 | Carlson |
| 2007/0088193 A1 | 4/2007 | Omori |
| 2007/0100206 A1 | 5/2007 | Lin |
| 2007/0106119 A1 | 5/2007 | Hirata |
| 2007/0118015 A1 | 5/2007 | Wendlandt |
| 2007/0142711 A1* | 6/2007 | Bayer ................ A61B 1/00016 600/175 |
| 2007/0149855 A1* | 6/2007 | Noguchi ............ A61B 1/00096 600/168 |
| 2007/0162095 A1 | 7/2007 | Kimmel |
| 2007/0167681 A1 | 7/2007 | Gill |
| 2007/0177008 A1 | 8/2007 | Bayer |
| 2007/0177009 A1 | 8/2007 | Bayer |
| 2007/0185384 A1 | 8/2007 | Bayer |
| 2007/0188427 A1 | 8/2007 | Lys |
| 2007/0197875 A1 | 8/2007 | Osaka |
| 2007/0203396 A1 | 8/2007 | McCutcheon |
| 2007/0206945 A1 | 9/2007 | DeLorme |
| 2007/0213591 A1 | 9/2007 | Aizenfeld |
| 2007/0229656 A1 | 10/2007 | Khait |
| 2007/0241895 A1 | 10/2007 | Morgan |
| 2007/0244353 A1 | 10/2007 | Larsen |
| 2007/0244354 A1 | 10/2007 | Bayer |
| 2007/0247867 A1 | 10/2007 | Hunter |
| 2007/0249907 A1 | 10/2007 | Boulais |
| 2007/0265492 A1 | 11/2007 | Sonnenschein |
| 2007/0270642 A1 | 11/2007 | Bayer |
| 2007/0279486 A1 | 12/2007 | Bayer |
| 2007/0286764 A1 | 12/2007 | Noguchi |
| 2007/0293720 A1 | 12/2007 | Bayer |
| 2008/0009673 A1 | 1/2008 | Khachi |
| 2008/0021274 A1 | 1/2008 | Bayer |
| 2008/0025413 A1 | 1/2008 | Apostolopoulos |
| 2008/0036864 A1 | 2/2008 | McCubbrey |
| 2008/0045797 A1 | 2/2008 | Yasushi |
| 2008/0058601 A1 | 3/2008 | Fujimori |
| 2008/0071290 A1 | 3/2008 | Larkin |
| 2008/0091065 A1 | 4/2008 | Oshima |
| 2008/0130108 A1 | 6/2008 | Bayer |
| 2008/0151070 A1 | 6/2008 | Shiozawa |
| 2008/0161646 A1 | 7/2008 | Gomez |
| 2008/0163652 A1 | 7/2008 | Shatskin |
| 2008/0167529 A1 | 7/2008 | Otawara |
| 2008/0177139 A1 | 7/2008 | Courtney |
| 2008/0183034 A1 | 7/2008 | Henkin |
| 2008/0183043 A1 | 7/2008 | Spinnler |
| 2008/0221388 A1 | 9/2008 | Seibel et al. |
| 2008/0246771 A1 | 10/2008 | O'Neal |
| 2008/0253686 A1 | 10/2008 | Bayer |
| 2008/0262312 A1 | 10/2008 | Carroll |
| 2008/0275298 A1 | 11/2008 | Ratnakar |
| 2008/0303898 A1 | 12/2008 | Nishimura |
| 2009/0005643 A1 | 1/2009 | Smith |
| 2009/0023998 A1 | 1/2009 | Ratnakar |
| 2009/0030275 A1 | 1/2009 | Nicolaou |
| 2009/0036840 A1* | 2/2009 | Viray .................. A61F 6/225 604/264 |
| 2009/0054790 A1 | 2/2009 | Czaniera |
| 2009/0062615 A1 | 3/2009 | Yamaya |
| 2009/0076327 A1 | 3/2009 | Ohki |
| 2009/0082624 A1 | 3/2009 | Joko |
| 2009/0082626 A1* | 3/2009 | Ichimura ........... A61B 1/00082 600/109 |
| 2009/0086017 A1 | 4/2009 | Miyano |
| 2009/0135245 A1 | 5/2009 | Luo |
| 2009/0137875 A1 | 5/2009 | Kitagawa |
| 2009/0143647 A1 | 6/2009 | Banju |
| 2009/0147076 A1 | 6/2009 | Ertas |
| 2009/0182917 A1 | 7/2009 | Kim |
| 2009/0213211 A1 | 8/2009 | Bayer |
| 2009/0216084 A1 | 8/2009 | Yamane |
| 2009/0225159 A1 | 9/2009 | Schneider |
| 2009/0231419 A1 | 9/2009 | Bayer |
| 2009/0234183 A1 | 9/2009 | Abe |
| 2009/0244361 A1* | 10/2009 | Gebauer ............. H04N 5/2253 348/373 |
| 2009/0253966 A1 | 10/2009 | Ichimura |
| 2009/0287188 A1 | 11/2009 | Golden |
| 2009/0287192 A1 | 11/2009 | Vivenzio |
| 2009/0299144 A1 | 12/2009 | Shigemori |
| 2010/0010309 A1 | 1/2010 | Kitagawa |
| 2010/0016673 A1 | 1/2010 | Bandy |
| 2010/0053312 A1 | 3/2010 | Watanabe |
| 2010/0069713 A1 | 3/2010 | Endo |
| 2010/0073470 A1 | 3/2010 | Takasaki |
| 2010/0073948 A1 | 3/2010 | Stein |
| 2010/0076268 A1 | 3/2010 | Takasugi |
| 2010/0123950 A1 | 5/2010 | Fujiwara |
| 2010/0130822 A1 | 5/2010 | Katayama |
| 2010/0141763 A1 | 6/2010 | Itoh |
| 2010/0160729 A1 | 6/2010 | Smith |
| 2010/0174144 A1 | 7/2010 | Hsu |
| 2010/0231702 A1 | 9/2010 | Tsujimura |
| 2010/0245653 A1 | 9/2010 | Bodor |
| 2010/0249513 A1 | 9/2010 | Tydlaska |
| 2010/0280322 A1 | 11/2010 | Mizuyoshi |
| 2010/0296178 A1 | 11/2010 | Genet |
| 2010/0326703 A1 | 12/2010 | Gilad |
| 2011/0004058 A1 | 1/2011 | Oneda |
| 2011/0004059 A1 | 1/2011 | Arneson |
| 2011/0034769 A1* | 2/2011 | Adair ................. H04N 5/3765 600/110 |
| 2011/0063427 A1 | 3/2011 | Fengler |
| 2011/0084835 A1 | 4/2011 | Whitehouse |
| 2011/0140003 A1 | 6/2011 | Beck |
| 2011/0160530 A1 | 6/2011 | Ratnakar |
| 2011/0160535 A1 | 6/2011 | Bayer |
| 2011/0169931 A1 | 7/2011 | Pascal |
| 2011/0184243 A1 | 7/2011 | Wright |
| 2011/0211267 A1 | 9/2011 | Takato |

(56) References Cited

U.S. PATENT DOCUMENTS

| | | |
|---|---|---|
| 2011/0254937 A1 | 10/2011 | Yoshino |
| 2011/0263938 A1 | 10/2011 | Levy |
| 2011/0282144 A1 | 11/2011 | Gettman |
| 2011/0292258 A1 | 12/2011 | Adler |
| 2012/0040305 A1 | 2/2012 | Karazivan |
| 2012/0050606 A1 | 3/2012 | Debevec |
| 2012/0053407 A1* | 3/2012 | Levy ............... A61B 1/00177 600/109 |
| 2012/0057251 A1 | 3/2012 | Takato |
| 2012/0065468 A1 | 3/2012 | Levy |
| 2012/0076425 A1 | 3/2012 | Brandt |
| 2012/0143004 A1* | 6/2012 | Gupta ............... A61B 1/00096 600/117 |
| 2012/0162402 A1 | 6/2012 | Amano |
| 2012/0200683 A1* | 8/2012 | Oshima ............ A61B 1/00009 348/65 |
| 2012/0209071 A1 | 8/2012 | Bayer |
| 2012/0209289 A1 | 8/2012 | Duque |
| 2012/0212630 A1 | 8/2012 | Pryor |
| 2012/0220832 A1 | 8/2012 | Nakade |
| 2012/0224026 A1 | 9/2012 | Bayer |
| 2012/0229615 A1 | 9/2012 | Kirma |
| 2012/0232340 A1 | 9/2012 | Levy |
| 2012/0232343 A1 | 9/2012 | Levy |
| 2012/0253121 A1 | 10/2012 | Kitano |
| 2012/0277535 A1 | 11/2012 | Hoshino |
| 2012/0281536 A1 | 11/2012 | Gell |
| 2012/0289858 A1 | 11/2012 | Ouyang |
| 2012/0300999 A1 | 11/2012 | Bayer |
| 2013/0050523 A1* | 2/2013 | Kodama ............ H04N 5/2253 348/222.1 |
| 2013/0053646 A1 | 2/2013 | Yamamoto |
| 2013/0057724 A1 | 3/2013 | Miyahara |
| 2013/0060086 A1 | 3/2013 | Talbert |
| 2013/0066297 A1 | 3/2013 | Shtul |
| 2013/0077257 A1 | 3/2013 | Tsai |
| 2013/0085329 A1 | 4/2013 | Morrissette |
| 2013/0109916 A1 | 5/2013 | Levy |
| 2013/0116506 A1 | 5/2013 | Bayer |
| 2013/0131447 A1 | 5/2013 | Benning |
| 2013/0137930 A1 | 5/2013 | Menabde |
| 2013/0141557 A1 | 6/2013 | Kawata |
| 2013/0150671 A1 | 6/2013 | Levy |
| 2013/0158344 A1 | 6/2013 | Taniguchi |
| 2013/0169843 A1 | 7/2013 | Ono |
| 2013/0172670 A1 | 7/2013 | Levy |
| 2013/0172673 A1* | 7/2013 | Kennedy, II ....... A61B 1/00073 600/109 |
| 2013/0172676 A1 | 7/2013 | Levy |
| 2013/0197309 A1 | 8/2013 | Sakata |
| 2013/0197556 A1 | 8/2013 | Shelton |
| 2013/0222640 A1 | 8/2013 | Baek |
| 2013/0253268 A1 | 9/2013 | Okada |
| 2013/0264465 A1 | 10/2013 | Dai |
| 2013/0267778 A1 | 10/2013 | Rehe |
| 2013/0271588 A1 | 10/2013 | Kirma |
| 2013/0274551 A1 | 10/2013 | Kirma |
| 2013/0281925 A1 | 10/2013 | Benscoter |
| 2013/0296649 A1 | 11/2013 | Kirma |
| 2013/0303979 A1 | 11/2013 | Stieglitz |
| 2013/0317295 A1 | 11/2013 | Morse |
| 2014/0018624 A1 | 1/2014 | Bayer |
| 2014/0031627 A1 | 1/2014 | Jacobs |
| 2014/0046136 A1 | 2/2014 | Bayer |
| 2014/0107418 A1 | 4/2014 | Ratnakar |
| 2014/0148644 A1 | 5/2014 | Levi |
| 2014/0184766 A1 | 7/2014 | Amling |
| 2014/0213850 A1 | 7/2014 | Levy |
| 2014/0225998 A1 | 8/2014 | Dai |
| 2014/0276207 A1 | 9/2014 | Ouyang |
| 2014/0296628 A1 | 10/2014 | Kirma |
| 2014/0296643 A1 | 10/2014 | Levy |
| 2014/0296866 A1 | 10/2014 | Salman |
| 2014/0298932 A1 | 10/2014 | Okamoto |
| 2014/0309495 A1 | 10/2014 | Kirma |
| 2014/0316198 A1 | 10/2014 | Krivopisk |
| 2014/0316204 A1 | 10/2014 | Ofir |
| 2014/0320617 A1 | 10/2014 | Parks |
| 2014/0333742 A1 | 11/2014 | Salman |
| 2014/0333743 A1 | 11/2014 | Gilreath |
| 2014/0336459 A1 | 11/2014 | Bayer |
| 2014/0343358 A1 | 11/2014 | Hameed |
| 2014/0343361 A1 | 11/2014 | Salman |
| 2014/0343489 A1 | 11/2014 | Lang |
| 2014/0364691 A1 | 12/2014 | Krivopisk |
| 2014/0364692 A1 | 12/2014 | Salman |
| 2014/0364694 A1 | 12/2014 | Avron |
| 2015/0005581 A1 | 1/2015 | Salman |
| 2015/0045614 A1 | 2/2015 | Krivopisk |
| 2015/0057500 A1 | 2/2015 | Salman |
| 2015/0094536 A1 | 4/2015 | Wieth |
| 2015/0099925 A1 | 4/2015 | Davidson |
| 2015/0099926 A1 | 4/2015 | Davidson |
| 2015/0105618 A1 | 4/2015 | Levy |
| 2015/0164308 A1 | 6/2015 | Ratnakar |
| 2015/0182105 A1 | 7/2015 | Salman |
| 2015/0196190 A1 | 7/2015 | Levy |
| 2015/0201827 A1 | 7/2015 | Sidar |
| 2015/0208900 A1 | 7/2015 | Vidas |
| 2015/0208909 A1 | 7/2015 | Davidson |
| 2015/0223676 A1 | 8/2015 | Bayer |
| 2015/0230698 A1 | 8/2015 | Cline |
| 2015/0272422 A1* | 10/2015 | Aoyama ............ A61B 1/00006 348/68 |
| 2015/0305601 A1 | 10/2015 | Levi |
| 2015/0313445 A1 | 11/2015 | Davidson |
| 2015/0313450 A1 | 11/2015 | Wieth |
| 2015/0313451 A1 | 11/2015 | Salman |
| 2015/0320300 A1 | 11/2015 | Gershov |
| 2015/0342446 A1 | 12/2015 | Levy |
| 2015/0359415 A1 | 12/2015 | Lang |
| 2015/0374206 A1 | 12/2015 | Shimony |
| 2016/0015257 A1 | 1/2016 | Levy |
| 2016/0015258 A1 | 1/2016 | Levin |
| 2016/0058268 A1 | 3/2016 | Salman |
| 2016/0143512 A1* | 5/2016 | Cheng ............... A61B 1/00128 600/123 |
| 2016/0166134 A1* | 6/2016 | Sonnenschein ...... H04N 5/2253 600/109 |
| 2016/0183843 A1* | 6/2016 | Conklin ............. A61F 2/2496 600/587 |
| 2016/0191863 A1* | 6/2016 | Minikey, Jr. ......... H04N 5/2252 348/148 |
| 2016/0213236 A1* | 7/2016 | Hruska ............. A61B 1/267 |
| 2016/0246048 A1 | 8/2016 | Ofir et al. |

FOREIGN PATENT DOCUMENTS

| | | |
|---|---|---|
| CA | 2812097 | 3/2012 |
| CA | 2798716 | 6/2013 |
| CA | 2798729 | 6/2013 |
| CN | 103348470 | 10/2013 |
| CN | 103403605 | 11/2013 |
| CN | 103491854 | 1/2014 |
| CN | 103702604 | 4/2014 |
| CN | 103732120 | 4/2014 |
| CN | 104717916 | 6/2015 |
| CN | 105246393 | 1/2016 |
| CN | 105324065 | 2/2016 |
| CN | 105324066 | 2/2016 |
| CN | 105338875 | 2/2016 |
| CN | 105358042 | 2/2016 |
| CN | 105358043 | 2/2016 |
| CN | 105377106 | 3/2016 |
| CN | 105407788 | 3/2016 |
| DE | 202010016900 | 5/2011 |
| EP | 1690497 | 8/2006 |
| EP | 1835844 | 9/2007 |
| EP | 1968425 | 9/2008 |
| EP | 1986541 | 11/2008 |
| EP | 1988813 | 11/2008 |
| EP | 2023794 | 2/2009 |

(56) References Cited

FOREIGN PATENT DOCUMENTS

| | | |
|---|---|---|
| EP | 2023795 | 2/2009 |
| EP | 2190341 | 6/2010 |
| EP | 2211683 | 8/2010 |
| EP | 2457492 | 5/2012 |
| EP | 2457493 | 5/2012 |
| EP | 1988812 | 11/2012 |
| EP | 2520218 | 11/2012 |
| EP | 2604175 | 6/2013 |
| EP | 2618718 | 7/2013 |
| EP | 2635932 | 9/2013 |
| EP | 2648602 | 10/2013 |
| EP | 2649648 | 10/2013 |
| EP | 2672878 | 12/2013 |
| EP | 2736400 | 6/2014 |
| EP | 2744390 | 6/2014 |
| EP | 2442706 | 11/2014 |
| EP | 2865322 | 4/2015 |
| EP | 2908714 | 8/2015 |
| EP | 2979123 | 2/2016 |
| EP | 2991537 | 3/2016 |
| EP | 2994032 | 3/2016 |
| EP | 2994033 | 3/2016 |
| EP | 2994034 | 3/2016 |
| EP | 2996536 | 3/2016 |
| EP | 2996541 | 3/2016 |
| EP | 2996542 | 3/2016 |
| EP | 2996621 | 3/2016 |
| GB | 12196628 | 3/2015 |
| JP | H1043129 | 2/1998 |
| JP | H10239740 | 9/1998 |
| JP | 11137512 | 5/1999 |
| JP | 2005253543 | 9/2005 |
| JP | 2006025888 | 2/2006 |
| JP | 2006068109 | 3/2006 |
| JP | 2010178766 A | 8/2010 |
| JP | 2012135432 | 7/2012 |
| JP | 2013116277 A2 | 6/2013 |
| JP | 2013123647 | 6/2013 |
| JP | 2013123648 | 6/2013 |
| JP | 2013208459 | 10/2013 |
| JP | 2013215582 | 10/2013 |
| JP | 2013230383 | 11/2013 |
| JP | 2013542467 | 11/2013 |
| JP | 2013544617 | 12/2013 |
| JP | 2014524303 | 9/2014 |
| JP | 2014524819 | 9/2014 |
| JP | 2015533300 | 11/2015 |
| WO | 2006073676 | 7/2006 |
| WO | 2006073725 | 7/2006 |
| WO | 2007070644 | 6/2007 |
| WO | 2007092533 | 8/2007 |
| WO | 2007092636 | 8/2007 |
| WO | 2007087421 | 11/2007 |
| WO | 2007136859 | 11/2007 |
| WO | 2007136879 | 11/2007 |
| WO | 2008015164 | 2/2008 |
| WO | 2009014895 | 1/2009 |
| WO | 2009015396 | 1/2009 |
| WO | 2009049322 | 4/2009 |
| WO | 2009049324 | 4/2009 |
| WO | 2009062179 | 5/2009 |
| WO | 2010146587 | 12/2010 |
| WO | 2012038958 | 3/2012 |
| WO | 2012056453 | 5/2012 |
| WO | 2012075153 A2 | 6/2012 |
| WO | 2012077116 | 6/2012 |
| WO | 2012077117 | 6/2012 |
| WO | 2012096012 | 7/2012 |
| WO | 2012120507 | 9/2012 |
| WO | 2013014673 | 1/2013 |
| WO | 2013024476 | 2/2013 |
| WO | 2014061023 | 4/2014 |
| WO | 2014160983 | 10/2014 |
| WO | 2014179236 | 11/2014 |
| WO | 2014182723 | 11/2014 |
| WO | 2014182728 | 11/2014 |
| WO | 2014183012 | 11/2014 |
| WO | 2014186230 | 11/2014 |
| WO | 2014186519 | 11/2014 |
| WO | 2014186521 | 11/2014 |
| WO | 2014186525 | 11/2014 |
| WO | 2014186775 | 11/2014 |
| WO | 2014210516 | 12/2014 |
| WO | 2015002847 | 1/2015 |
| WO | 2015047631 | 4/2015 |
| WO | 2015050829 | 4/2015 |
| WO | 2015084442 | 6/2015 |
| WO | 2015095481 | 6/2015 |
| WO | 2015112747 | 7/2015 |
| WO | 2015112899 | 7/2015 |
| WO | 2015134060 | 9/2015 |
| WO | 2015168066 | 11/2015 |
| WO | 2015168664 | 11/2015 |
| WO | 2015171732 | 11/2015 |
| WO | 2015175246 | 11/2015 |
| WO | 2016014581 | 1/2016 |
| WO | 2016033403 | 3/2016 |

OTHER PUBLICATIONS

Office Action dated Jun. 26, 2016 for U.S. Appl. No. 14/278,293.
Office Action dated Jul. 1, 2016 for U.S. Appl. No. 14/229,699.
Office Action dated Jul. 15, 2016 for U.S. Appl. No. 14/273,923.
Notice of Allowance dated Jul. 15, 2016 for U.S. Appl. No. 14/274,323.
Office Action dated Jul. 22, 2016 for U.S. Appl. No. 14/549,265.
Sherman L.M., Plastics That Conduct Hear, Plastice Technology, Jun. 2001—article obtained online from http://www.ptonline.com/articles/plastics-that-conduct-heat.
Office Action dated Aug. 11, 2016 for U.S. Appl. No. 14/318,248.
Office Action dated Apr. 28, 2016 for U.S. Appl. No. 13/912,014.
Notice of Allowance dated Aug. 26, 2016 for U.S. Appl. No. 13/212,627.
Office Action dated Sep. 2, 2016 for U.S. Appl. No. 14/278,338.
Office Action dated Sep. 16, 2016 for U.S. Appl. No. 13/992,014.
Notice of Allowance dated Oct. 12, 2016 for U.S. Appl. No. 13/119,032.
Office Action dated Oct. 7, 2016 for U.S. Appl. No. 13/713,449.
Office Action dated Oct. 5, 2016 for U.S. Appl. No. 14/271,270.
Notice of Allowance dated Oct. 13, 2016 for U.S. Appl. No. 14/273,923.
Notice of Allowance dated Nov. 9, 2016 for U.S. Appl. No. 13/557,114.
Office Action dated Dec. 1, 2016 for U.S. Appl. No. 14/278,293.
Office Action dated Dec. 9, 2016 for U.S. Appl. No. 14/549,265.
Office Action dated Dec. 16, 2016 for U.S. Appl. No. 14/263,896.
Notice of Allowance dated Dec. 28, 2016 for U.S. Appl. No. 14/229,699.
Notice of Allowance dated Dec. 27, 2016 for U.S. Appl. No. 14/317,863.
Office Action dated Dec. 27, 2016 for U.S. Appl. No. 14/603,137.
Office Action dated Dec. 29, 2016 for U.S. Appl. No. 15/077,513.
Office Action dated Dec. 30, 2016 for U.S. Appl. No. 14/457,268.
Office Action dated Jan. 17, 2017 for U.S. Appl. No. 14/318,189.
Notice of Allowance dated Jan. 31, 2017 for U.S. Appl. No. 14/271,234.
Office Action dated Feb. 2, 2017 for U.S. Appl. No. 14/278,338.
Office Action dated Feb. 9, 2017 for U.S. Appl. No. 14/746,986.
Office Action dated Feb. 6, 2017 for U.S. Appl. No. 14/751,835.
Office Action dated Feb. 14, 2017 for U.S. Appl. No. 14/271,270.
Office Action dated Feb. 23, 2017 for U.S. Appl. No. 14/318,249.
Office Action dated Mar. 9, 2017 for U.S. Appl. No. 14/791,316.
Office Action dated Mar. 21, 2017 for U.S. Appl. No. 13/992,014.
Office Action dated Mar. 20, 2017 for U.S. Appl. No. 14/278,293.
Notice of Allowance dated Mar. 21, 2017 for U.S. Appl. No. 14/649,265.
Office Action dated Mar. 22, 2017 for U.S. Appl. No. 14/705,355.
Office Action dated Mar. 24, 2017 for U.S. Appl. No. 14/638,509.

(56) References Cited

OTHER PUBLICATIONS

Notice of Allowance dated Apr. 12, 2017 for U.S. Appl. No. 14/503,137.
Notice of Allowance dated Apr. 18, 2017 for U.S. Appl. No. 13/713,449.
Office Action dated Apr. 19, 2017 for U.S. Appl. No. 14/918,551.
Notice of Allowability dated Apr. 21, 2017 for U.S. Appl. No. 14/549,265.
Office Action dated May 11, 2017 for U.S. Appl. No. 14/278,293.
Office Action dated May 10, 2017 for U.S. Appl. No. 14/918,551.
Office Action dated May 5, 2017 for U.S. Appl. No. 15/077,513.
Notice of Allowance dated May 15, 2017 for U.S. Appl. No. 14/271,270.
Office Action dated May 15, 2017 for U.S. Appl. No. 14/278,293.
Office Action dated May 18, 2017 for U.S. Appl. No. 14/278,338.
Notice of Allowance dated May 16, 2017 for U.S. Appl. No. 14/746,986.
Office Action dated May 23, 2017 for U.S. Appl. No. 13/655,120.
Notice of Allowance dated May 25, 2017 for U.S. Appl. No. 14/318,189.
Office Action dated May 23, 2017 for U.S. Appl. No. 14/560,975.
International Search Report for PCT/US14/37004, dated Sep. 25, 2014.
International Search Report for PCT/US2014/037526, dated Oct. 16, 2014.
International Search Report for PCT/US14/38094, dated Nov. 6, 2014.
International Search Report for PCT/US2015/012751, dated Jun. 26, 2015.
International Search Report for PCT/US2014/58143, dated Jan. 21, 2015.
International Search Report for PCT/US2014/071085, dated Mar. 27, 2015.
International Search Report for PCT/US2015/027902, dated Jul. 23, 2015.
International Search Report for PCT/US2015/012506, dated Dec. 11, 2015.
International Search Report for PCT/US2015/29421, dated Aug. 7, 2015.
International Search Report for PCT/US2015/28962, dated Jul. 28, 2015.
International Search Report for PCT/US2015/47334, dated Dec. 28, 2015.
International Search Report for PCT/US2015/41396, dated Sep. 29, 2015.
International Search Report for PCT/US2015/66486, dated Dec. 17, 2015.
International Search Report for PCT/US2015/6548, dated Feb. 26, 2016.
Office Action dated Feb. 26, 2016 U.S. Appl. No. 14/274,323.
Office Action dated Feb. 4, 2016 by U.S. Appl. No. 14/271,234.
Corrected Notice of Allowance dated Apr. 13, 2016 for U.S. Appl. No. 13/680,646.
Notice of Allowance dated Mar. 28 2016 for U.S. Appl. No. 13/413,059.
Notice of Allowance dated Mar. 29, 2016 for U.S. Appl. No. 13/680,646.
Office Action dated Mar. 23, 2016 for U.S. Appl. No. 13/713,449.
Office Action dated Mar. 24, 2016 for U.S. Appl. No. 13/212,627.
Office Action dated Mar. 28 2016 for U.S. Appl. No. 13/119,032.
Office Action dated Mar. 25 2016 for U.S. Appl. No. 14/271,234.
Office Action dated May 5, 2016 for U.S. Appl. No. 14/278,338.
Office Action dated May 6, 2016 for U.S. Appl. No. 14/263,896.

* cited by examiner

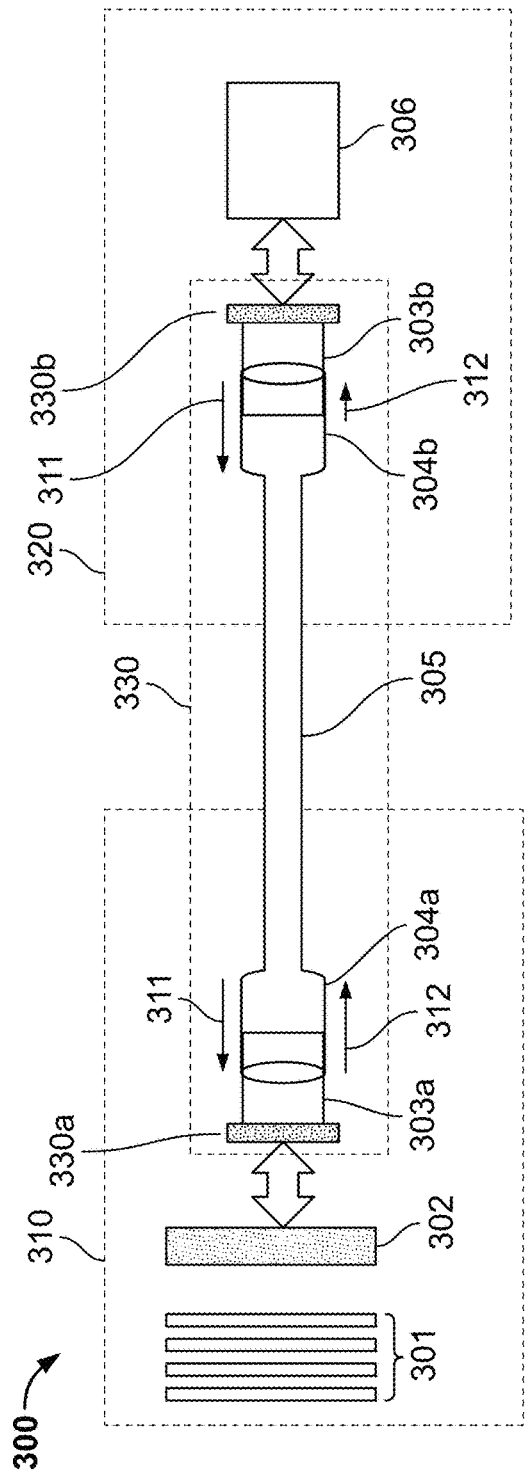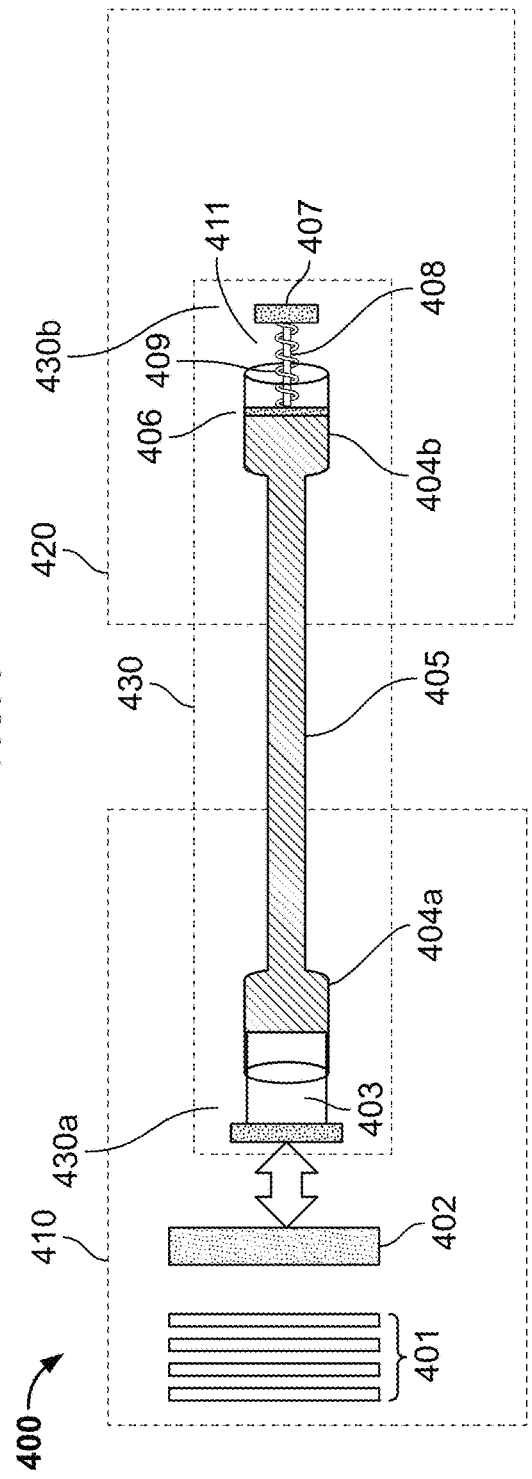
FIG. 3
FIG. 4

SYSTEMS AND METHODS FOR IMAGE MAGNIFICATION USING RELATIVE MOVEMENT BETWEEN AN IMAGE SENSOR AND A LENS ASSEMBLY

CROSS-REFERENCE TO RELATED APPLICATIONS

This application is a continuation application of U.S. patent application Ser. No. 15/074,807, filed on Mar. 18, 2016, which claims the benefit of priority to U.S. Patent Provisional Application No. 62/134,742, filed on Mar. 18, 2015.

Each of the above-mentioned applications is herein incorporated by reference in its entirety.

FIELD

The present specification relates generally to systems for enhancing the magnification power or zoom capability of optical devices, and more specifically those which are used in medical devices, such as endoscopes.

BACKGROUND

Medical probes such as endoscopes are used for examining and treating internal body structures such as the alimentary canals, airways, the gastrointestinal system, and other organ systems. Endoscopes have attained great acceptance within the medical community since they provide a means for performing procedures with minimal patient trauma, while enabling the physician to view the internal anatomy of the patient. Over the years, numerous endoscopes have been developed and categorized according to specific applications, such as cystoscopy, colonoscopy, laparoscopy, upper gastrointestinal (GI) endoscopy and others. Endoscopes may be inserted into the body's natural orifices or through an incision in the skin.

An endoscope usually comprises an elongated tubular shaft, rigid or flexible, having a video camera or a fiber optic lens assembly at its distal end. The shaft is connected to a handle, which sometimes includes an ocular lens or eyepiece for direct viewing. Viewing is also usually possible via an external screen. Various surgical tools may be inserted through a working channel in the endoscope for performing different surgical procedures.

In an electronic endoscopy system, the main control unit, which is used to process data from an endoscope, is generally a separate unit while the endoscope itself is a device that can be attached to the main control unit. The main control unit comprises a front panel and/or a display screen for displaying operational information with respect to an endoscopy procedure when the endoscope is in use. The display screen may be configured to display images and/or video streams received from the viewing elements of the multiple viewing elements endoscope.

In recent years, there has been an increasing demand for improving the image quality of medical probes, such as endoscopes, to enhance in the accuracy of a diagnosis. A majority of the endoscopic devices available in the market have limited magnification power. During an endoscopic procedure, physicians often want to focus on a specific area in the human body to analyze the same in more detail. They are, however, constrained by the limited magnification power of the endoscopic devices to enlarge or zoom an area of interest. The technical limitations as a result of the small size of endoscopic devices make it difficult to dynamically enhance magnification power in these devices.

Usually, in a typical, non-endoscope imaging apparatus, dynamic image magnification is achieved by either moving the complete objective lens assembly or through relative motion between specific groups of lenses. In an endoscopic device, usually, it is not possible to move the complete objective lens assembly as the barrel surrounding the lens assembly is fixed within the endoscope so that it can be appropriately sealed.

In conventional objective lens systems, the magnification is achieved by relative motion between separate groups of lenses. In such systems, a lens group is moved to change a state of the objective optical system suitable for normal observation state into a state of the objective optical system suitable for close-up observation so that the objective optical system is closer to a particular object optionally selected from a plurality of objects present in an observation area by an observer to make it possible to observe the particular object in detail. In endoscopy systems, because of the miniature size of such devices, providing activators for enabling movement of separate groups of the lens assembly as described above makes the overall system very complicated and hence it is not possible to provide a very high magnification capability in such devices. The conventional endoscopy systems are thus usually constrained as far as their as their magnification power is concerned.

There is a need for addressing the above-mentioned limitation in medical probes, such as endoscopes, to enhance the quality of medical procedures conducted using such devices. There is a need for providing endoscope systems with dynamic magnification capabilities which are easy to implement in a miniaturized environment and have a robust structure.

SUMMARY

The present specification discloses an endoscope comprising: a proximal end comprising a control portion; a distal end comprising a distal tip, wherein said distal tip comprises at least one objective lens assembly and at least one sensor configured to receive images captured by said objective lens assembly; an insertion tube extending between the proximal end and distal end; and, a magnification control system comprising a first end positioned at the proximal end, a second end positioned at the distal end and a channel extending between the first end and second end, wherein said first end comprises a first member positioned within the channel, wherein said second end comprises a second member positioned within the channel and physically coupled to the sensor, and wherein the magnification control system is configured such that movement of the first member causes a corresponding movement of the second member and sensor.

Optionally, the channel is a first cylindrical unit, wherein the first member is a first hub, wherein the second member is a second hub, and wherein the second hub is coupled to the sensor and the first hub is coupled to a user control unit, further wherein the channel is an air tight closed system. Optionally, the second hub is coupled to the sensor through a printed circuit board which is located on a horizontal portion of the sensor. Optionally, the user control unit is adapted to generate a signal that causes an actuator to move the first hub in a proximal or distal direction and thereby communicate a pressure change to the second member, causing a movement of the second hub which translates into a corresponding movement of the sensor coupled to the second hub. Still optionally, the channel is filled with a fluid and configured to be a fluid closed system such that no fluid is permitted to pass outside the channel and beyond the first hub or second hub. Optionally, said magnification control system has a first level of magnification capability and a second level of magnification capability, wherein the first level of magnification capability is defined by the sensor being located in a first position and the second level of magnification capability is defined by the sensor being in a second position such that the second position is further from the objective lens assembly than the first position.

At the first position, distance of the sensor from the objective lens may range from 0.7 mm to 1.7 mm and, at the second position, distance of the sensor from the objective lens may range from 1.8 mm to 2.7 mm. At the first position, the sensor may be at a distance ranging from 1 mm to 1.2 mm from the objective lens assembly and at the second position the sensor device may be at a distance of 1.3 mm from the objective lens assembly. The magnification control system may be adapted to move the sensor from the first position to the second position in incremental steps of 0.01 mm.

Optionally, the channel comprises a first cylindrical unit coupled to a piston based controller on a proximal end and a second hub on a distal end, and said piston based controller comprises a piston coupled to a control switch through a connecting rod and a spring. Optionally, said control portion, first end and first member are located in a handle portion of the endoscope and said second end and second member are located in said distal tip.

The present specification also discloses an endoscope comprising: a lens assembly, wherein said lens assembly comprises a plurality of lenses; a sensor configured to receive images captured by said lens assembly; and, a magnification control system coupled to said sensor comprising a first cylindrical unit coupled to a first hub and a second cylindrical unit coupled to a second hub, wherein the first cylindrical unit and second cylindrical unit are connected through an air-tight tube, wherein the first hub is coupled to a user control unit and the second hub is coupled to the sensor, and wherein the magnification control system is configured such that movement of the first hub translates into movement of the second hub and sensor device through a change in air pressure in the air-tight tube.

Optionally, the first cylindrical unit and second cylindrical unit in combination with the tube comprise a fluid tight closed system. Optionally, the second hub is coupled to the sensor device through a printed circuit board which is located on a horizontal portion of the sensor. Optionally, said magnification control system has a first level of magnification capability and a second level of magnification capability, wherein the first level of magnification capability is defined by the sensor being located in a first position and the second level of magnification capability is defined by the sensor being in a second position such that the second position is further from the lens assembly than the first position.

The present specification also discloses an endoscope with an image magnification capability comprising: a distal tip section comprising a plurality of objective lenses, a sensor configured to receive images captured by said plurality of objective lenses, and at least one expandable and retractable connector coupling the sensor to a lens holder and facilitating a movement of the sensor across a plurality of predefined positions; and a magnification control system coupled to said sensor enabling said movement of the sensor relative to a position of said plurality of objective lenses to provide varying levels of magnification capability, wherein said magnification control system comprises a first unit coupled to a first hub located in a control handle portion of the endoscope and a second unit coupled to a second hub located in the distal tip section of the endoscope, wherein the first unit and second unit are connected through an air-tight tube, having a first level of air pressure, extending from said control handle portion to said distal tip section, and wherein said second hub is coupled to the sensor and the first hub is coupled to a user control system.

Optionally, said expandable and retractable connector comprises a curved bended structure. Optionally, said sensor comprises a vertical portion, a first horizontal portion and a second horizontal portion.

Optionally, the endoscope further comprises a second expandable and retractable connector, wherein said first horizontal portion comprises a first housing to accommodate a movement of the at least one expandable and retractable connector and said second horizontal portion comprises a second housing to accommodate a movement of the second expandable and retractable connector.

The present specification also discloses a method of operating an endoscope comprising a distal tip with an objective lens assembly and a sensor configured to receive images captured by said objective lens assembly, a control handle, an insertion tube extending between the distal tip and control handle, and a magnification control system comprising a first end in the control handle, a second end in the distal tip and coupled to the sensor, and a fluid-tight channel extending through the insertion tube and between the first end and second, the method comprising: at the control handle, receiving an input to change a magnification level; in response to said input, causing a pressure level at the first end to change; and as a result of the pressure level change, communicating said pressure level change through the fluid-tight channel to the second end, wherein said pressure level change causes the second end to move and, correspondingly, the sensor to move, thereby altering a distance between the sensor and the objective lens assembly by an amount determined by said input.

Optionally, increasing the distance between the sensor and the objective lens assembly by a predetermined unit in response to the input increases a magnification of the endoscope. Optionally, decreasing the distance between the sensor and the objective lens assembly by a predetermined unit in response to the input decreases a magnification of the endoscope.

The present specification also discloses an imaging optical system comprising: an objective lens assembly; a sensor device configured for receiving the images formed by said objective lens assembly; and, a magnification control system coupled to said sensor device such that the magnification control system enables the movement of sensor device relative to the position of said objective lens assembly to provide varying levels of magnification capability. Optionally, said magnification control system comprises a first cylindrical unit coupled to a first hub and a second cylindrical unit coupled to a second hub, wherein the two cylindrical units are connected through a tube and wherein the first hub is coupled to the sensor device and the second hub is coupled to a user control unit. Optionally, the two cylindrical units along with the tube comprise an air tight closed system. Optionally, the first hub is coupled to the sensor device through a printed circuit board which is located on a horizontal portion of the sensor device, and application of pressure through the user control unit causes movement of the second hub and wherein said movement of the second hub translates into a corresponding movement of first hub and the sensor device coupled to the first hub.

Optionally, a space between the two cylindrical units and the tube is filled with a fluid such as water, oil, alcohol, air. Optionally, said imaging system has two levels of magnification capability, a first magnification stage in which the sensor device is located in a first position and an increased magnification stage in which the sensor device is positioned in a second position such that the second position is further from the objective lens than the first position. At the first position the sensor device may be at a distance of 1.2 mm from the lens assembly and at the second position the sensor device may be at a distance of 2.2 mm from the lens assembly. At the first position the sensor device may be at a distance of 1 mm from the lens assembly and at the second position the sensor device may be at a distance of 1.3 mm from the lens assembly. The sensor device may be moved from the first position to the second position in incremental steps of 0.01 mm. Optionally, said imaging system has a plurality of levels of magnification capability.

The imaging optical system may be used in a medical probe such as an endoscope. Optionally, said tube is manufactured using fiber material or plastic. Optionally, said first hub and said second hub are in an air tight configuration with the corresponding cylindrical units. Optionally, the magnification control system comprises a first cylindrical unit coupled to a first hub and a second cylindrical unit coupled to a piston based controller, wherein the two cylindrical units are connected through a tube and wherein the first hub is coupled to the sensor device. Optionally, said piston based controller comprises a piston coupled to a control switch through a connecting rod and a spring.

The present specification also discloses an imaging optical system comprising: an objective lens assembly, wherein said objective lens assembly comprises a plurality of objective lenses; a sensor device configured for receiving the images formed by said objective lens assembly; and, a magnification control system coupled to said sensor device comprising a first cylindrical unit coupled to a first hub and a second cylindrical unit coupled to a second hub, wherein the two cylindrical units are connected through an air-tight tube, wherein the first hub is coupled to the sensor device and the second hub is coupled to a user control unit, and wherein movement of the second hub translates into movement of the first hub and sensor device through a change in air pressure in the air-tight tube.

The present specification also discloses an endoscope with an imaging optical system comprising: an objective lens assembly, wherein said objective lens assembly comprises a plurality of objective lenses; a sensor device configured for receiving the images formed by said plurality of objective lens; and, a magnification control system coupled to said sensor device such that the magnification control system enables the movement of sensor device relative to the position of said plurality of objective lens to provide different levels of magnification capability.

Optionally, the magnification control system comprises a first cylindrical unit coupled to a first hub and a second cylindrical unit coupled to a second hub, wherein the two cylindrical units are connected through a tube and wherein the first hub is coupled to the sensor device and the second hub is coupled to a user control unit. Optionally, said plurality of objective lens and said sensor device are located in a tip section of an insertion tube of said endoscope. Optionally, said first cylindrical unit and said first hub are located in a tip section of an insertion tube and said second cylindrical unit and said second hub are located in a handle portion of the endoscope. Optionally, the two cylindrical units along with the tube comprise an air tight closed system.

Optionally, the first hub is coupled to the sensor device through a printed circuit board which is located on a horizontal portion of the sensor device. Optionally, when pressure is applied through the user control unit, the second hub moves, wherein movement of the second hub translates into a corresponding movement of first hub and the sensor device coupled to the first hub. Optionally, a space between the two cylindrical units and the tube is filled with a fluid such as water, oil, alcohol, air. Optionally, said endoscope has two levels of magnification capability, a regular magnification stage in which the sensor device is located in a first position and an enhanced magnification stage in which is sensor device is positioned in a second position such that the second position is further from the objective lens than the first position.

Optionally, said tube is manufactured using fiber-optic material or plastic. Optionally, said first hub and said second hub are in an air tight configuration with the corresponding cylindrical units. Optionally, the magnification control system comprises a first cylindrical unit coupled to a first hub and a second cylindrical unit coupled to a piston based controller, wherein the two cylindrical units are connected through a tube and wherein the first hub is coupled to the sensor device. Optionally, said piston based controller comprises a piston coupled to a control switch through a connecting rod and a spring.

The present specification also discloses an endoscope with dynamic image magnification capability comprising: a distal tip section comprising a plurality of objective lenses, a sensor device configured for receiving the images formed by said plurality of objective lenses, and at least one dynamic connector coupling the sensor device to a circuit board and facilitating the movement of sensor device across a plurality of predefined positions by accordingly adjusting its own position; and a magnification control system coupled to said sensor device enabling a movement of sensor device relative to a position of said objective lenses to provide varying levels of magnification capability said magnification control system comprising a first cylindrical unit coupled to a first hub located in the distal tip section and a second cylindrical unit coupled to a second hub located in a control handle portion of the endoscope wherein the first and second cylindrical units are connected through an air-tight tube, having a first level of air pressure, running through an insertion tube section of the endoscope and wherein said first hub is coupled to said sensor device and the second hub is coupled to a user control system. Optionally, said dynamic connector comprises a curved bended structure. Optionally, said sensor device comprises a vertical portion, a first horizontal portion and a second horizontal portion.

Optionally, said first horizontal portion comprises a first housing to accommodate the movement of a first dynamic connector across a plurality of predefined positions and said second horizontal portion comprises a second housing to accommodate the movement of a second dynamic portion across a plurality of predefined positions.

The present specification also discloses an endoscope with dynamic image magnification capability comprising: a distal tip section comprising a plurality of objective lenses, a sensor device configured for receiving the images formed by said plurality of objective lenses, and at least one dynamic connector coupling the sensor device to a circuit board and facilitating the movement of sensor device across a plurality of predefined positions by accordingly adjusting its own position; and, a magnification control system coupled to said sensor device enabling the movement of sensor device relative to the position of said objective lenses to provide varying levels of magnification capability said magnification control system comprising a first cylindrical unit coupled to a hub located in the distal tip section and a second cylindrical unit coupled to a piston controller located in a control handle portion of the endoscope wherein the two cylindrical units are connected through a tube running through an insertion tube section of the endoscope and wherein said hub is coupled to said sensor device and said piston controller comprises a piston coupled to a control switch through a connecting rod and a spring.

Optionally, said dynamic connector comprises a curved bended structure. Optionally, said sensor device comprises a vertical portion, a first horizontal portion and a second horizontal portion. Optionally, said first horizontal portion comprises a first housing to accommodate the movement of a first dynamic connector across a plurality of predefined positions and said second horizontal portion comprises a second housing to accommodate the movement of a second dynamic portion across a plurality of predefined positions.

The present specification also discloses a method of operating an imaging optical system comprising: an objective lens assembly; a sensor device configured for receiving the images formed by said objective lens assembly; and, a magnification control system coupled to said sensor device such that the magnification control system enables the movement of sensor device relative to the position of said objective lens assembly to provide varying levels of magnification capability; the method comprising: providing input to change existing magnification level; and altering distance between the sensor device and the objective lens assembly by a predetermined unit in response to the input. Optionally, increasing the distance between the sensor device and the objective lens assembly by a predetermined unit in response to the input increases magnification capability of the imaging system. Optionally, decreasing the distance between the sensor device and the objective lens assembly by a predetermined unit in response to the input decreases magnification capability of the imaging system.

The aforementioned and other embodiments of the present shall be described in greater depth in the drawings and detailed description provided below.

BRIEF DESCRIPTION OF THE DRAWINGS

These and other features and advantages of the present invention will be appreciated, as they become better understood by reference to the following detailed description when considered in connection with the accompanying drawings, wherein:

FIG. 3 is a schematic diagram of an endoscopy system with a magnification control system in accordance with an embodiment of the present specification;

FIG. 4 is a schematic diagram of an endoscopy system with a magnification control system in accordance with another embodiment of the present specification;

DETAILED DESCRIPTION

Figure 1A:
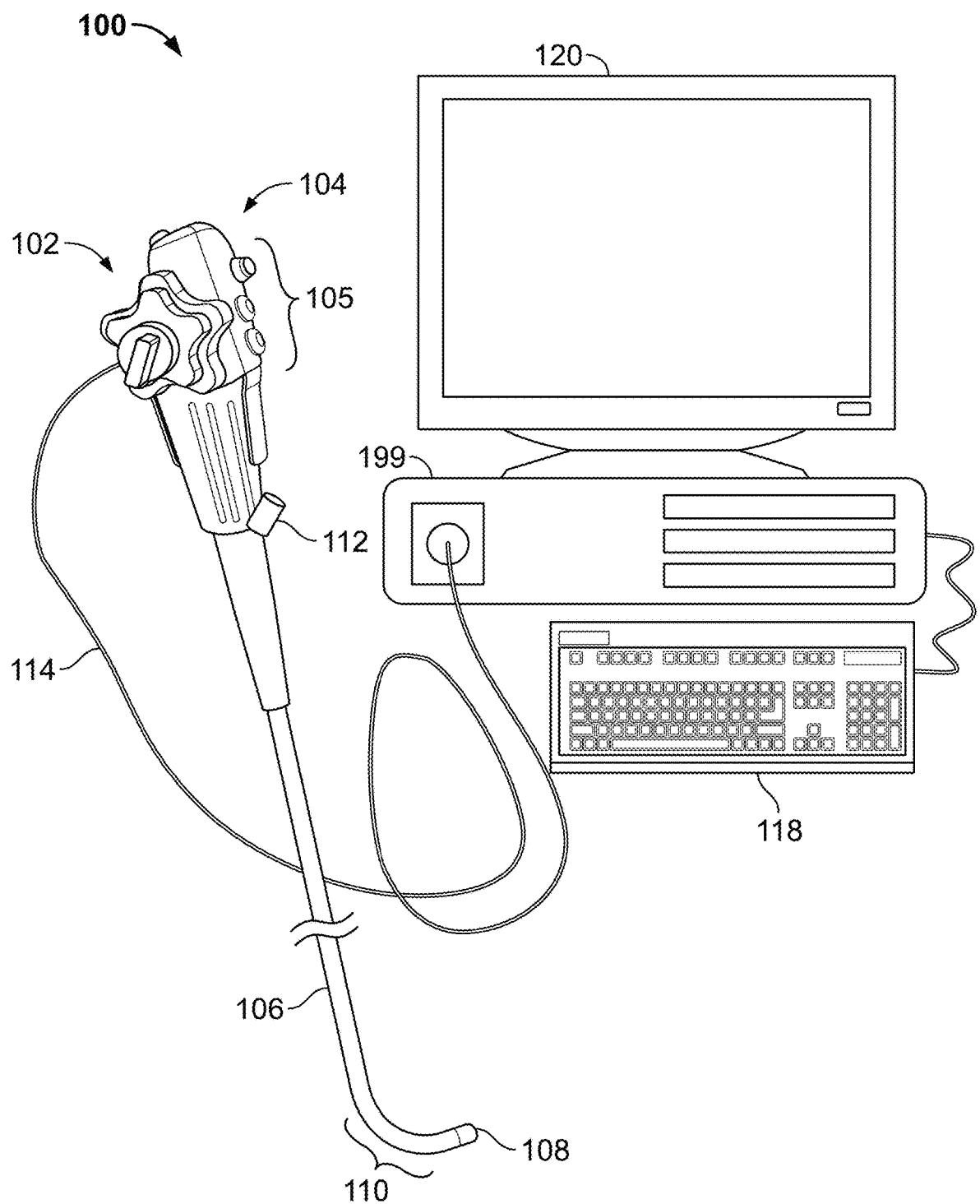
FIG. 1A illustrates a view of a multiple viewing elements endoscopy system, according to some embodiments of the present specification.

The present specification is directed towards a system for enabling dynamic image magnification in optical imaging devices which are used in high performance and critical applications, such as medical procedures. Physicians often require a very close view of the internal anatomy while conducting invasive medical procedures. However, the size of devices used in medical procedures, especially invasive endoscopic procedures, is very small and hence it is very difficult to provide dynamic image magnification capability in such devices.

Usually, in any imaging apparatus, image magnification is achieved either through the movement of the complete objective lens assembly or through the relative motion between separate groups of lenses comprising the objective lens assembly. In an endoscopic device, it is usually not possible or practical to move the complete objective lens assembly as the barrel surrounding the lens assembly is fixed within the endoscope housing for providing a tight seal. Further, because of the miniature size of such devices, providing activators for enabling movement of separate lens' groups of the lens assembly is very complicated and not easy to implement.

In an embodiment, the present specification is directed towards an imaging system comprising a lens assembly and a sensor which can be moved relative to the lens assembly.

In an embodiment, the movement between the lens assembly and sensor is employed to achieve dynamic image magnification or optical zoom.

In embodiments, the present specification relates to U.S. patent application Ser. No. 13/882,004, entitled "Optical Systems for Multi-Sensor Endoscopes" and filed on Apr. 26, 2013. In embodiments, the present specification relates to U.S. patent application Ser. No. 15/051,834, entitled "Optical System for An Endoscope" and filed on Feb. 24, 2016. The above-mentioned applications are incorporated by reference herein in their entirety.

In an embodiment, the present specification is directed towards an endoscope system comprising an optical lens assembly and a sensor device wherein based upon at least one user instruction to zoom an image, the sensor device is moved relative to the objective lens assembly to provide image magnification. In an embodiment, the sensor device is moved farther from the objective lens assembly to provide image magnification. In other embodiments, using different optical lenses, the sensor device is moved closer relative to the objective lens assembly to provide image magnification.

In an embodiment, the present specification describes an endoscopy device comprising a magnification control system coupled to an image sensor for controlling the position of the image sensor relative to the objective lens assembly based on the level of image magnification (or zoom) required by a user.

In an embodiment, the position of the image sensor device can be changed incrementally to enable multiple levels of image magnification. In another embodiment, the present specification describes an endoscope device with a two-stage magnification capability wherein in a first or standard magnification stage, the image sensor device is in a first or normal position and in a second magnification stage, and the sensor device is in a second position which is further from the objective lens assembly, magnifying the view.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

Image capturing devices may be Charged Coupled Devices (CCD's) or Complementary Metal Oxide Semiconductor (CMOS) image sensors, or other suitable devices having a light sensitive surface usable for capturing an image. In some embodiments, a sensor such as a Charge Coupled Device (CCD) or a Complementary Metal Oxide Semiconductor (CMOS) image sensor (for detecting the reflected light received by an optical element), is employed.

As used in the specification, the term "optical assembly" is used to describe a set of components that allows the endoscopic device to capture light and transform that light into at least one image. In some embodiments, lenses/optical elements are employed to capture light and image capturing devices, such as sensors, are employed to transform that light into data representative of at least one image. In some embodiments, an optical element comprises a plurality of optics such as lens assemblies, lenses and protective glass, and is configured to receive reflected light from target objects.

An optical assembly, as used in the specification, comprises at least one lens assembly, its associated sensor(s), and its associated circuit board. In some embodiments, an "optical assembly" may comprise more than one viewing element or camera, associated sensor(s), and associated circuit board(s). In some embodiments, an "optical assembly" may comprise a front viewing element, its associated sensor, and its associated circuit board. In some embodiments, an "optical assembly" may comprise a front viewing element, its associated sensors, and its associated circuit board and/or at least one side viewing element, its associated sensors and its associated circuit boards. Further, the optical assembly typically is associated with at least one illuminator for illuminating the field of view. Thus, for example, a front-pointing optical assembly includes a front-pointing viewing element with a sensor and a circuit board and is associated with at least one illuminator.

Reference is now made to FIG. 1A, which shows a multiple viewing elements endoscopy system 100. System 100 may include a multiple viewing elements endoscope 102. Multiple viewing elements endoscope 102 may include a handle 104, from which an elongated shaft 106 emerges. Elongated shaft 106 terminates with a tip section 108 which is turnable by way of a bending section 110. Handle 104 may be used for maneuvering elongated shaft 106 within a body cavity. The handle 104 may include one or more buttons and/or knobs and/or switches 105 which control bending section 110 as well as functions such as fluid injection and suction. Handle 104 may further include at least one, and in some embodiments, one or more working channel openings 112 through which surgical tools may be inserted.

A utility cable 114, also referred to as an umbilical tube, may connect between handle 104 and a main control unit 199. Utility cable 114 may include therein one or more fluid channels and one or more electrical channels. The electrical channel(s) may include at least one data cable for receiving video signals from the front and side-pointing viewing elements, as well as at least one power cable for providing electrical power to the viewing elements and to the discrete illuminators.

The main control unit 199 contains the controls required for displaying the images of internal organs captured by the endoscope 102. The main control unit 199 may govern power transmission to the endoscope's 102 tip section 108, such as for the tip section's viewing elements and illuminators. The main control unit 199 may further control one or more fluid, liquid and/or suction pump(s) which supply corresponding functionalities to the endoscope 102. One or more input devices 118, such as a keyboard, a touch screen and the like may be connected to the main control unit 199 for the purpose of human interaction with the main control unit 199. In the embodiment shown in FIG. 1A, the main control unit 199 is connected to a screen/display 120 for displaying operation information concerning an endoscopy procedure when the endoscope 102 is in use. The screen 120 may be configured to display images and/or video streams received from the viewing elements of the multiple viewing elements endoscope 102. The screen 120 may further be operative to display a user interface for allowing a human operator to set various features of the endoscopy system.

Optionally, the video streams received from the different viewing elements of the multiple viewing elements endoscope 102 may be displayed separately on at least one monitor/screen 120 by uploading information from the main control unit 199, either side-by-side or interchangeably (namely, the operator may switch between views from the different viewing elements manually). Alternatively, these video streams may be processed by the main control unit 199 to combine them into a single, panoramic video frame, based on an overlap between fields of view of the viewing elements. In an embodiment, two or more displays may be connected to the main control unit 199, each for displaying a video stream from a different viewing element of the multiple viewing elements endoscope 102.

Figure 1B:
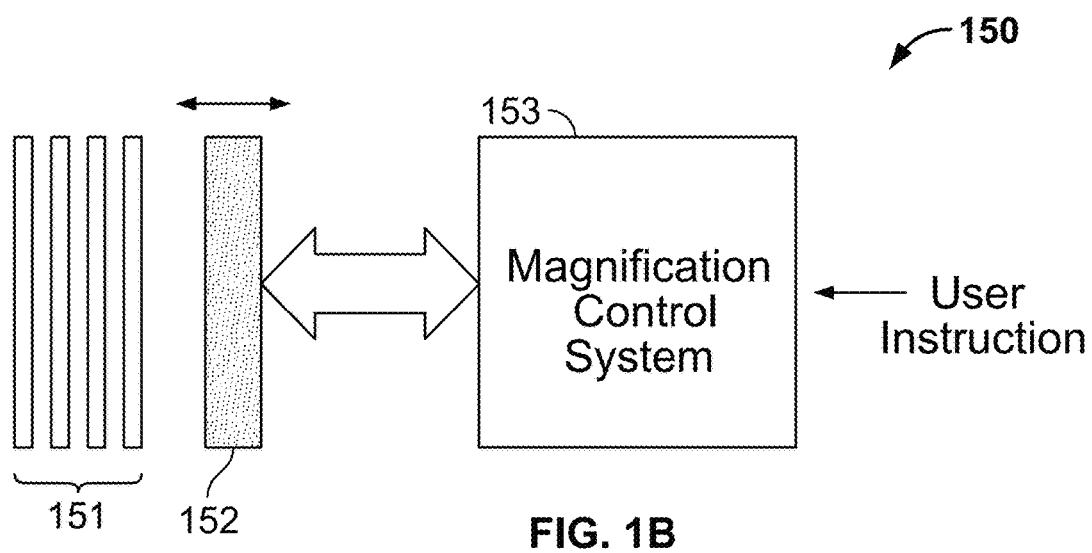
FIG. 1B illustrates a block diagram of an imaging system, in accordance with an embodiment of the present specification.

FIG. 1B is a block diagram of an imaging system in accordance with an embodiment of the present specification. As shown in FIG. 1B, imaging system 150 comprises a lens assembly 151, which includes at least one lens, and preferably a plurality of lenses. Lens assembly 151 is coupled to a sensor device or image sensor 152. In an embodiment, the sensor device 152 comprises an image capture device such as a CCD (charge-coupled device) which receives light radiation through the lens assembly 151 and captures the corresponding image information. In other embodiments, other image capture devices such as Complementary Metal Oxide Semiconductor (CMOS) sensors may also be used. An imaging system comprising a CMOS sensor is illustrated in FIG. 2C. In an embodiment, the sensor device 152 is coupled to a magnification control system 153. The magnification control system 153 controls the magnification capability of the imaging system 150 based upon at least one user instruction.

In an embodiment, the magnification control system 153 controls the position of sensor device 152 such that sensor device 152 is moved relative to the plurality of lenses or lens assembly 151 to change the magnification of the imaging system 150. In an embodiment, sensor device 152 can be moved incrementally away from objective lens assembly 151 to magnify the image at varying incremental levels. One of ordinary skill in the art would appreciate that the distance by which a sensor device is moved relative to the objective lens assembly can be configured as per the magnification requirement. In various embodiments, the sensor device is configured to move in increments ranging from 0.1 mm to 1.0 mm and is adapted to move from a first position to a second position such that the distance between the lens assembly 151 and the sensor device 152 ranges from 0.07 mm to 1.7 mm in the first position and from 1.8 mm to 2.7 mm in the second position. In an embodiment, the sensor device is configured to move in increments ranging from 0.01 mm to 0.1 mm and is adapted to move such that the distance between lens assembly 151 and sensor device 152 ranges from 0.01 mm to 1.0 mm. In one embodiment, a change in distance results in a linear change in magnification; for example, a distance of 0.2 mm results in a 2× change in magnification. In another embodiment, changes in distance results in a non-linear change in magnification.

In some embodiments, the movement of sensor device 152 is from a first position to a second position such that when sensor device 152 is in a first or standard position the imaging system 150 provides regular or normal (1×) magnification power (such as would be provided with the lens assembly 151 and sensor device without the use of the magnification control system 153) and when the sensor device 152 is in a second position, which is proximally away from, inward from, or otherwise at a greater distance from the objective lens assembly 151, the imaging system 150 provides enhanced magnification power. In embodiments, a distance between the lens assembly 151 and the first position of the sensor device 152 is in a range of 0.01 mm to 1.7 mm whereas a distance between the lens assembly 151 and the second/farthest position of the sensor device 152 is 1.8 mm to 2.7 mm, with other positions being between 0.01 mm and 1 mm and all increments therein.

One of ordinary skill in the art can appreciate that there may be multiple ways to control the movement of sensor device 152. In an embodiment, the magnification control system 153 comprises an electrical motor based system coupled to the sensor device 152 which controls the position of the sensor device 152. In another embodiment, the magnification control system 153 comprises a mechanical system which is used to control the movement of sensor device 152.

In an embodiment, the sensor device 152 is coupled to an image processing system which is used to process the image information captured by the sensor device 152 and display it on a screen for user viewing.

Figure 2A:
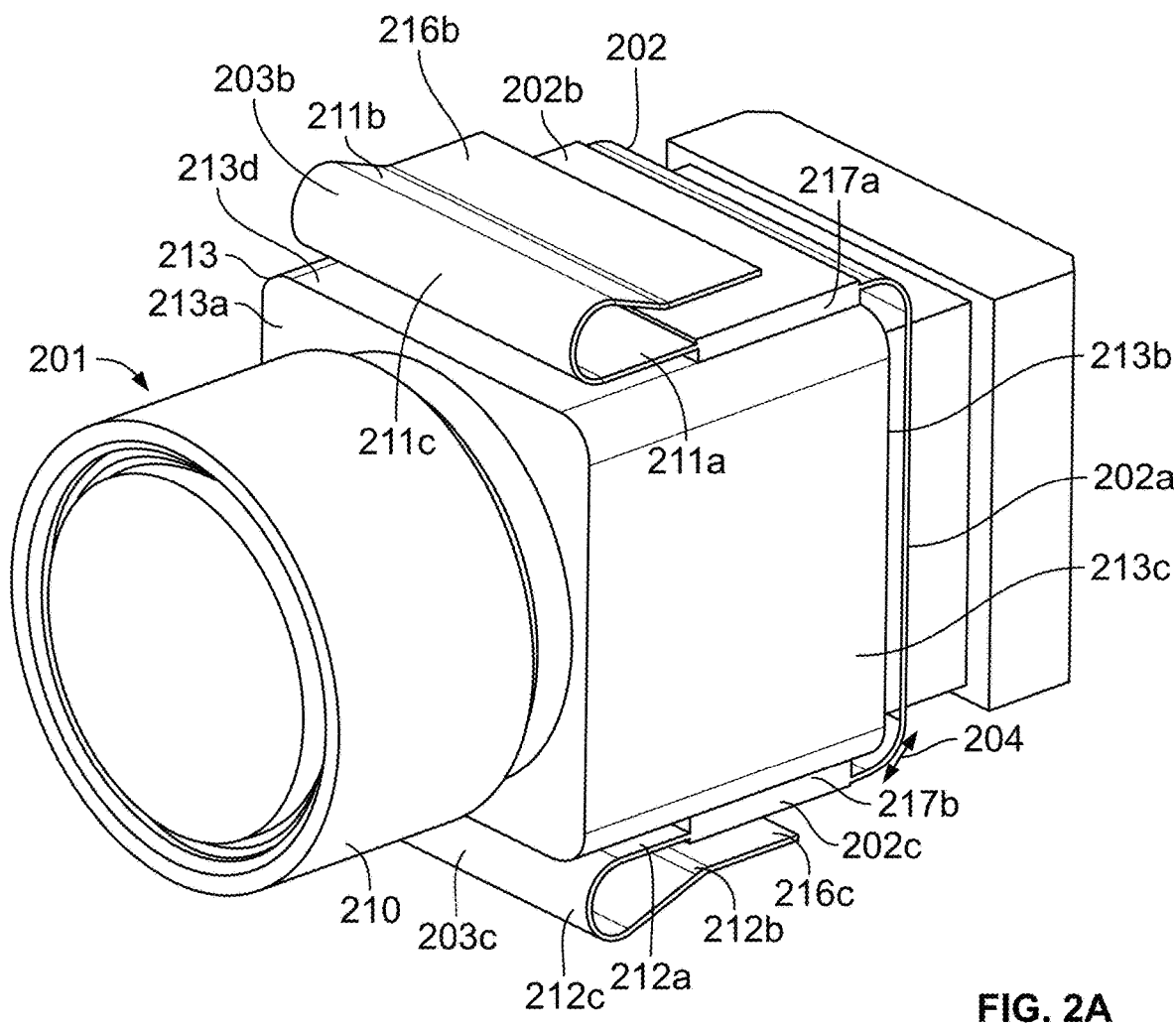
FIG. 2A illustrates an objective lens assembly, coupled with an image sensor, in accordance with an embodiment of the present specification.

FIG. 2A illustrates an objective lens assembly, coupled with an image sensor or sensor device, in accordance with an embodiment of the present specification. As shown in FIG. 2A, the objective lens assembly 201, comprising at least one lens, is coupled to sensor device 202 such that sensor device 202 is adapted to receive and capture images formed by the objective lens assembly 201. In an embodiment as shown in FIG. 2A, sensor device 202 comprises a solid state image pick up device such as a charge-coupled device (CCD). In another embodiment, as described with respect to FIG. 2C below, the sensor device 252 comprises a solid state image pick up device such as a Complementary Metal Oxide Semiconductor (CMOS) image sensor or other suitable device having a light sensitive surface usable for capturing an image.

Referring back to FIG. 2A, the lens assembly 201 comprises a lens holder 213, which in an embodiment, is rectangular and has a distal wall 213a, a first side wall 213c, a second opposing side wall (not visible in FIG. 2A), a top wall 213d and an opposing bottom wall (not visible in FIG. 2A); and a cylindrical portion 210 protruding distally from the distal wall 213a. Lens holder 213 comprises one or more lenses positioned therein.

In the embodiment shown in FIG. 2A, the sensor device 202 comprises a vertical portion 202a, arranged perpendicularly to a first horizontal portion 202b and a second horizontal portion 202c. The first and second horizontal portions 202b, 202c are parallel and are separated by a distance equal to the length of the vertical portion 202a as shown in FIG. 2A wherein the first horizontal portion 202b and second horizontal portion 202c serve as image sensor contact areas.

In an embodiment, vertical portion 202a includes an inner glass surface which is closely associated with a proximal wall 213b of lens holder 213. Also, the first and second horizontal portions 202b, 202c are closely associated with the top wall 213d and the bottom wall of the lens assembly 201, respectively, such that the sensor device 202 envelops the lens holder portion 213 of the lens assembly 201 on three sides, as shown in FIG. 2A. In the assembled position as shown in FIG. 2A, lens assembly 201 includes a plurality of objective lenses that are positioned inside the lens holder 213. In an embodiment, the cylindrical portion 210 of the lens assembly 201 projects in a distal direction extending beyond the area defined by the image sensor contact areas 202b and 202c.

In an embodiment as shown in FIG. 2A, each of the horizontal sections 202b and 202c are coupled at their respective first ends to vertical portion 202a and are coupled, at their second ends, with folded over or bent portions 203b and 203c, respectively, which facilitate the movement of the sensor device 202 relative to lens assembly 201. In an embodiment, second ends of horizontal sections 202b, 202c are coupled with folded over portions 203b, 203c respectively in such a manner that the folded over portions are movable with respect to the horizontal sections 202b, 202c. In embodiments, the position of folded over portion 203b may be arranged such that the folded over portion 203b protrudes distally beyond the second end of horizontal section 202b either entirely or partially. Similarly, the position of folded over portion 203c may be arranged such that the folded over portion 203c protrudes distally beyond the second end of horizontal section 202c either entirely or partially. In other embodiments, the folded over portions 203b and 203c are respectively connected to connecting portions 216b and 216c which connect the sensor device 202 to the printed circuit boards of the endoscope device.

The folded over portions 203b and 203c of the image sensor 202 reduce the length of space occupied by the lens assembly 201 and sensor device 202 on a circuit board placed in an endoscope tip, thereby enabling additional optical assemblies to be placed closer to each other than would have been possible with conventional methods of folding the image sensor. This reduces the distance between additional optical assemblies, which in turn, causes them to occupy approximately 1.3 mm less space on the endoscope circuit board, thereby leading to the diameter of the endoscope tip being reduced.

In some embodiments, the present specification relates to U.S. patent application Ser. No. 14/469,481, entitled "Circuit Board Assembly of A Multiple Viewing Elements Endoscope", filed on Aug. 26, 2014. In some embodiments, the present specification relates to U.S. Patent Provisional Application No. 62/299,332, entitled "Circuit Board Assembly of a Multi-Viewing Element Endoscope Using CMOS Sensors", and filed on Feb. 24, 2016. The above-mentioned applications are herein incorporated by reference in their entirety.

One of ordinary skill in the art can appreciate that there may be multiple ways to structure the bent or folded over portions 203b and 203c without departing from the spirt and scope of present specification. In an embodiment, the folded over dynamic portions 203b and 203c are structured such that they comprise a curved bent portion coupled to two flat portions on either side. As shown in FIG. 2A, the folded over dynamic portion 203b comprises a first flat portion 211a which is coupled to the second end of image sensor contact area 202b on one side and to a curved bent portion 211c on the other side. The curved portion 211c is in turn connected to a second flat portion 211b which is coupled with the connecting portion 216b which couples the sensor device with the circuit board. In an embodiment, connecting portion 216b is welded to the circuit board. Similarly, the folded over dynamic portion 203c comprises a first flat portion 212a which is coupled to the second end of image sensor contact area 202c on one side and to a curved bent portion 212c on the other side. The curved portion 212c is in turn connected to a second flat portion 212b which is coupled with the connecting portion 216c which couples the sensor device with the circuit board. In an embodiment, connecting portion 216c is welded to the circuit board. In an embodiment, each complete folded over dynamic portion 203b, 203c comprising first and second flat portions 211a, 211b, 212a, 212b, and curved portions 211c, 212c and the respective connecting portions 216b, 216c are manufactured in the form of a unitary structure. Further, the folded over dynamic portions 203b and 203c are configured to allow electrical coupling between the image sensor contact areas 202b, 202c and the circuit board. In an embodiment, the folded over dynamic portions 203b and 203c comprise embedded electrical wires that connect the image sensor contact areas 202b and 202c with the circuit board.

Figure 2B:
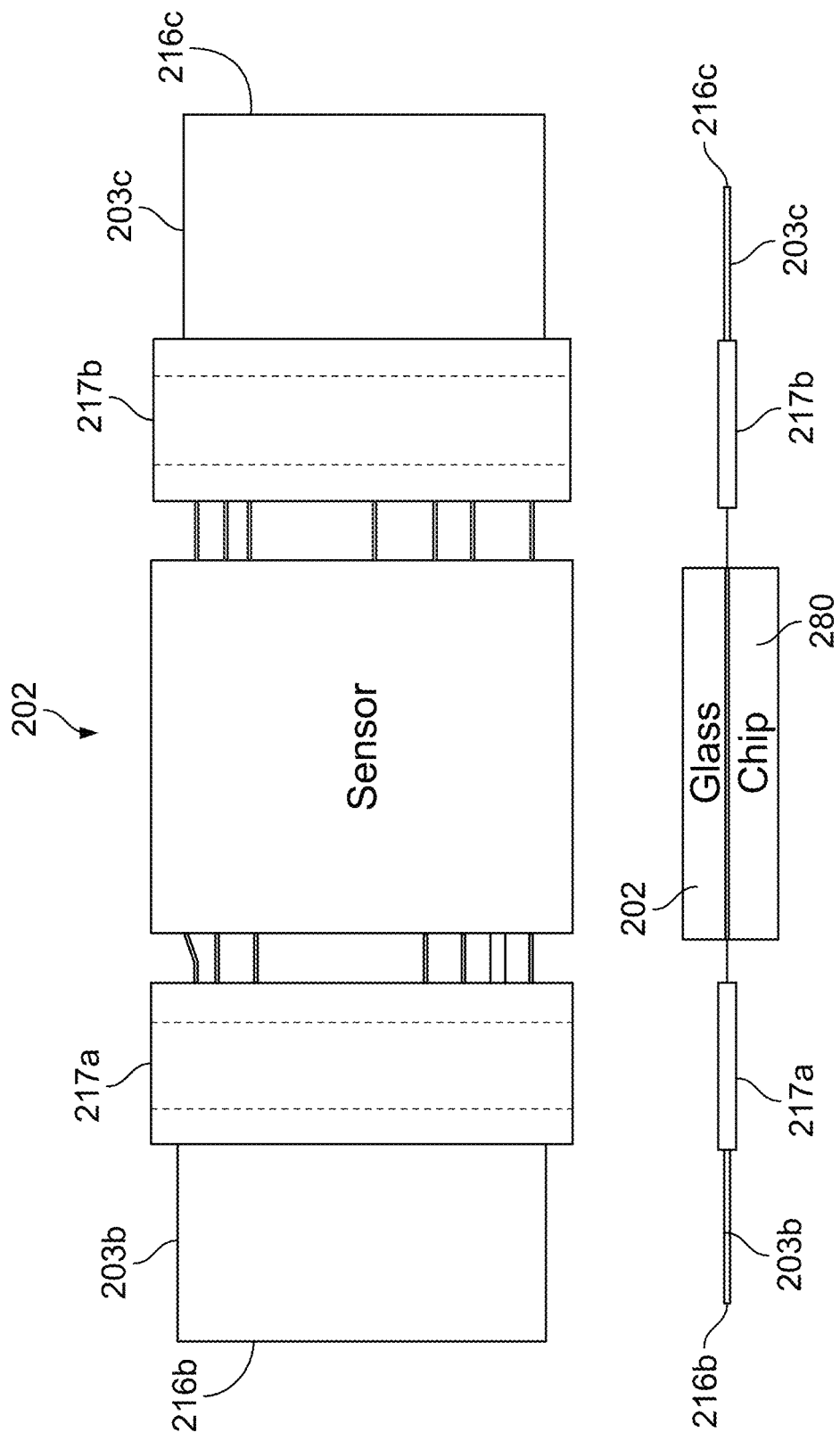
FIG. 2B illustrates an exemplary block diagram of a Charged Coupled Device (CCD) image sensor comprising connections for connecting with a circuit board, in accordance with an embodiment of the present specification.
Figure 2C:
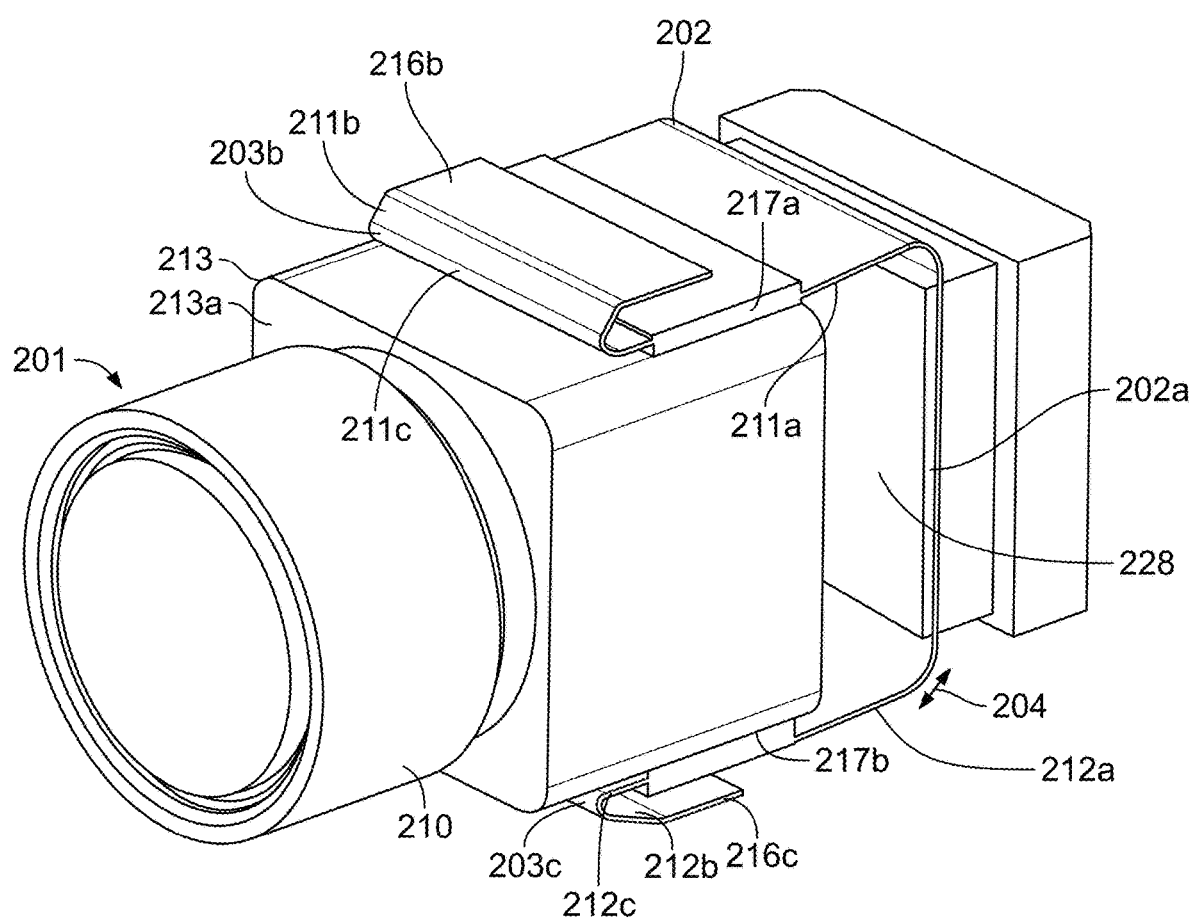
FIG. 2C illustrates the image sensor of FIG. 2A in a second position relative to the objective lens assembly.

In some embodiments, sensor 202 also comprises connector strips 217a, 217b that extend from the first ends of horizontal sections 202b, 202c to their second ends respectively. The connector strips 217a, 217b include openings configured to allow the flat portions 211a, 212a of the folded over dynamic portions 203b and 203c to move proximally and distally through the respective connector strips 217a, 217b as the sensor 202 is moved relative to the lens assembly 201. FIG. 2B illustrates an exemplary block diagram of a CCD image sensor comprising connections for connecting with a circuit board, in accordance with an embodiment of the present specification. Sensor 202 comprises connector strips 217a and 217b extending on either sides of sensor 202. Connector strip 217a enables movement of the sensor 202 as dynamic portion 203b folds and moves through connector strip 217a relative to fixed connecting portion 216b. Similarly, connector strip 217b enables movement of the sensor 202 as dynamic portion 203c folds and moves through connector strip 217b relative to fixed connecting portion 216c. Connecting portions 216b, 216c are connected to circuit board 280 by any suitable process, such as but not limited to, welding.

One of ordinary skill in the art can appreciate that a variety of materials can be used to manufacture the composite structure as illustrated here. Referring again to FIG. 2A, the composite structure comprising vertical wall 203A and dynamic portions 203b and 203c enable the movement of the sensor device 202 along an axis of the objective lens assembly 201.

In an embodiment, the sensor device 202 is coupled to a magnification control system which controls the position of the sensor device 202 such that the magnification power of the objective lens assembly 201 can be dynamically modified through movement of the sensor device 202 relative to the objective lens assembly 201. In an embodiment, the sensor device 202 is configured such that it can be moved proximally from a first position being closest to the objective lens assembly 201 to a second position at a distance farther from the objective lens assembly 201 and a plurality of incremental positions therebetween. In an embodiment, each of the horizontal sections 202b and 202c of the sensor device 202 are configured such that they comprise folded over dynamic portions 203b and 203c respectively, as described earlier, which facilitate the movement of the sensor device 202 between the positions.

In an embodiment, referring to FIG. 2A, in a first position the folded over dynamic portion 203b protrudes completely and distally outside the connector strip 217a and folded over dynamic portion 203c protrudes completely and distally outside the connector strip 217b, thereby bringing the sensor 202 closest to the objective lens assembly 201. FIG. 2C illustrates the image sensor 202 of FIG. 2A in a second position relative to the objective lens assembly 201. In the second position, the folded over dynamic portions 203b and 203c are positioned within or are retracted into connector strips 217a, 217b respectively, i.e. the folded over portions 203b and 203c protrude out only partially beyond the distal ends of connector strips 217a, 217b respectively, thereby taking the sensor 202 farthest away from the objective lens assembly 201. In the second position, the first flat portions 211a, 212a of the folded over dynamic portions 203b and 203c have moved proximally through the connector strips 217a, 217b relative to said connector strips 217a, 217b and connecting portions 216b, 216c. When moving the sensor 202 from the first position, as illustrated in FIG. 2A, to the second position, relative to the lens assembly 201, the sensor 202, vertical portion 202a, first flat portions 211a, 212a, and curved portions 211c, 212c all move in a proximal direction relative to the connector strips 217a, 217b, connecting portions 216b, 216c, and lens holder 213 and cylindrical portion 210 of the lens assembly 201, all of which are fixed. The first flat portions 211a, 212a bound, above and below respectively, a space 228 between the sensor 202 and lens assembly 201. In addition, when moving the sensor 202 from the first position, as illustrated in FIG. 2A, to the second position, relative to the lens assembly 201, the second flat portions 211b, 212b moved inwardly, toward the lens holder 213, to facilitate movement of the curved portions 211c, 212c into the connector strips 217a, 217b. In an embodiment, in the second position, the sensor device 202 is positioned further from the objective lens assembly 201 compared to the relative distance between the sensor device and objective lens assembly in the first position and hence the image magnification power of the device is higher in the second position as compared to the magnification power in first position. By controlling the distance between the sensor device 202 and the objective lens assembly 201, the system of the present specification allows dynamic change in image magnification power of the device. In an embodiment, the magnification power of the device can be increased by a power of 2× by moving the sensor device from a first position to a second position as described above. In an embodiment, the movement of the sensor device 202 is facilitated by a pressure controlled system as described below.

In various embodiments, the sensor device can be structured to enable movement incrementally across multiple positions to achieve multiple levels of magnification power. In some embodiments, the movement of the sensor device 202 relative to the lens assembly 201 ranges from 0.01 to 1.7 mm in the first position to 1.8 to 2.7 mm in the second position in increments of 0.01 mm or greater. The movement and user operations are described below with respect to FIGS. 5C and 5D.

Figure 2D:
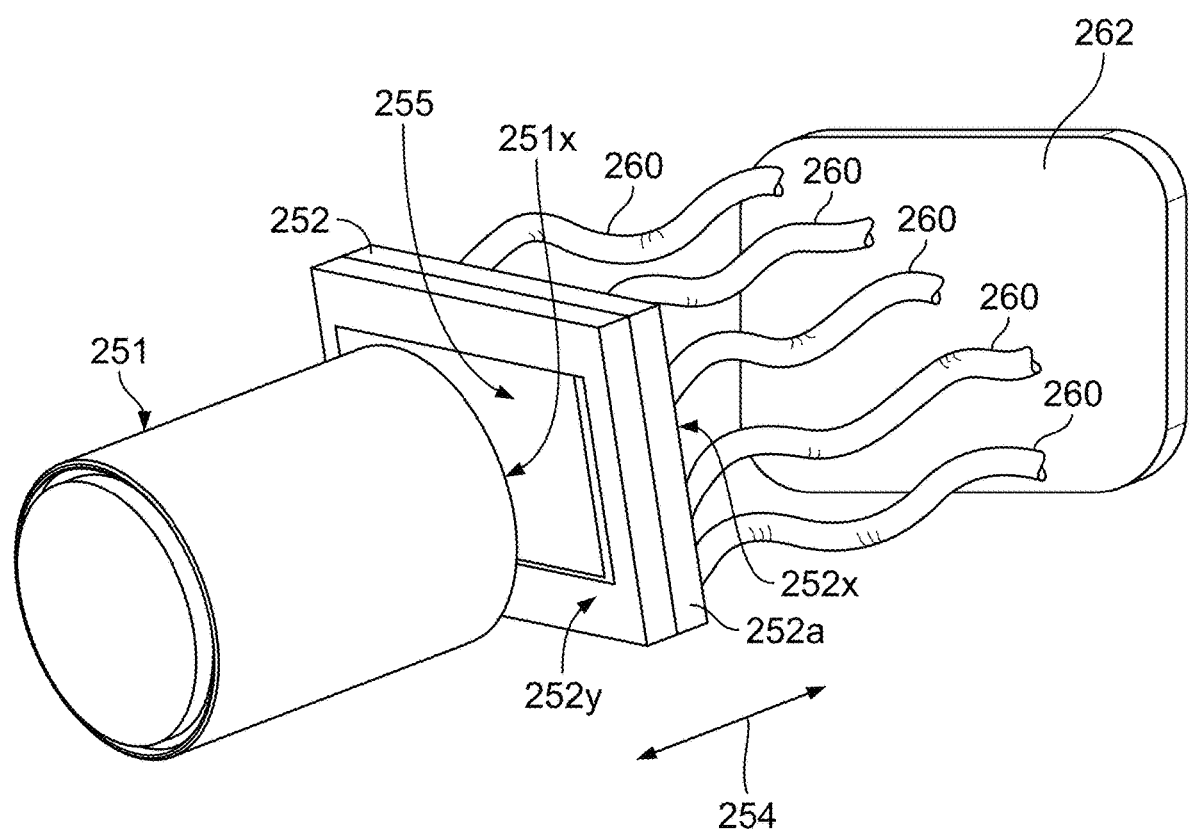
FIG. 2D illustrates an objective lens assembly, coupled with an image sensor, in accordance with an embodiment of the present specification.

FIG. 2D illustrates an alternate embodiment of the objective lens assembly, coupled with an image sensor wherein the sensor device comprises a solid state image pick up device such as a Complementary Metal Oxide Semiconductor (CMOS) image sensor or other suitable device having a light sensitive surface usable for capturing an image. As shown in FIG. 2D, the objective lens assembly 251, comprising at least one lens, is positioned proximate sensor device 252 such that sensor device 252 is adapted to receive and capture the images formed by the objective lens assembly 251. In an embodiment, the sensor device 252 comprises a vertical portion 252a having a proximal face 252x and a distal face 252y positioned proximate a proximal end 251x of cylindrical lens assembly 251. In an embodiment, distal face 252y comprises an inner glass surface 255 which is associated with proximal end of cylindrical lens assembly 251. In the objective lens assembly shown in FIG. 2D, in an embodiment, the sensor device 252 comprises flexible CMOS pins 260 which are coupled via their distal ends to the proximal face 252x of vertical portion 252a of the sensor device 252. The proximal ends of the CMOS pins 260 are attached to a circuit board 262 of the endoscope. The CMOS pins 260 are configured as flexible pins such that they allow the dynamic movement of sensor device 252, relative to the stationary lens assembly 251, to control the magnification power of device. As the sensor device 252 is moved along an axis of the objective lens assembly (through a magnification control system which is discussed in the subsequent sections) to modify the magnification power of the optical device, the flexible pins 260 allow the movement of sensor device 252 without snapping the connection between the pins 260 and sensor device 202 or the connection between the pins 260 and the endoscope circuit board 262. In an embodiment, the distance 254 represents the distance range of the dynamic movement of the sensor device 252 relative to the objective lens assembly 251.

Figure 2E:
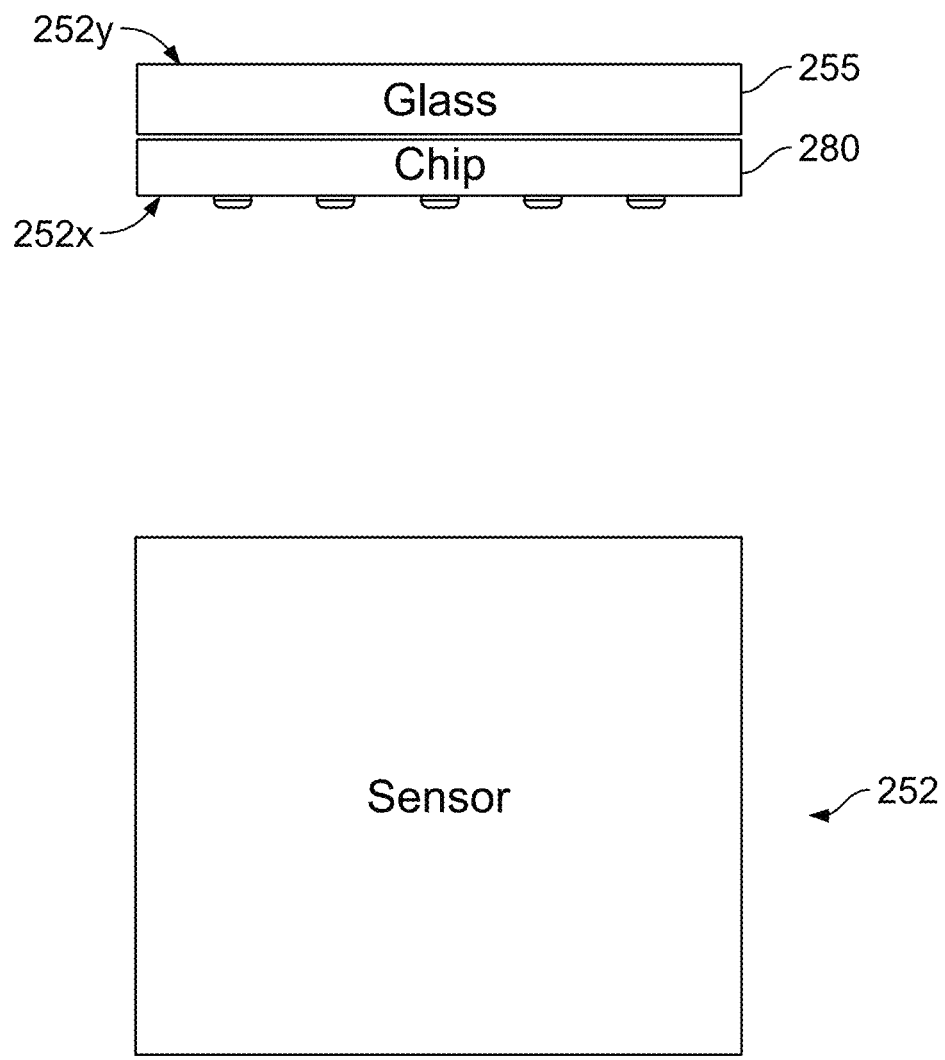
FIG. 2E illustrates an exemplary block diagram of a Complementary Metal Oxide Semiconductor (CMOS) image sensor comprising a glass surface connected with a circuit board, in accordance with an embodiment of the present specification.

FIG. 2E illustrates an exemplary block diagram of a CMOS image sensor comprising a glass surface connected with a circuit chip, in accordance with an embodiment of the present specification. CMOS sensor 252 comprises a glass surface 255 having a distal face 252y which faces the proximal end of cylindrical lens assembly 251, as shown in FIG. 2D; and a proximal face 252x comprising a sensor chip 280.

Figure 2F:
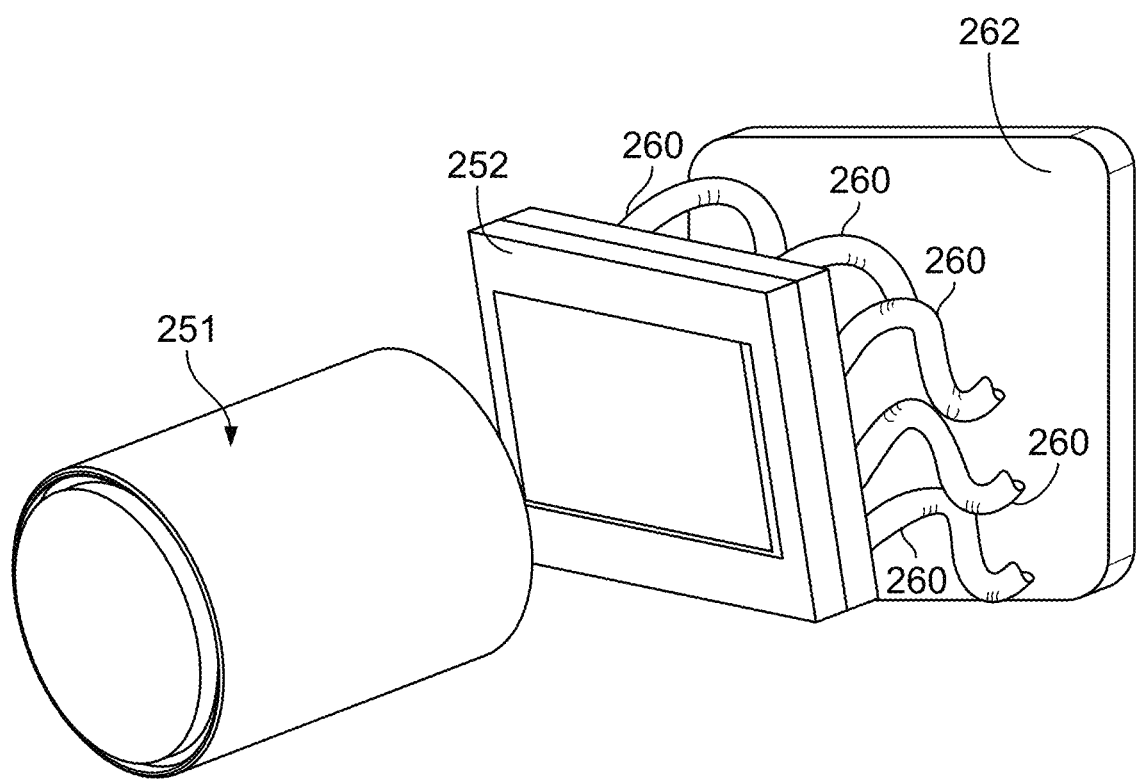
FIG. 2F illustrates the image sensor of FIG. 2D in a second position relative to the objective lens assembly.

FIG. 2F illustrates the image sensor 252 of FIG. 2D in a second position relative to the objective lens assembly 251. The image sensor 252 has been moved proximally such that it is farther away from the optical assembly 251 but closer to the circuit board 262. The flexible pins 260 can be seen in a more compressed configuration relative to the more extended configuration of the pins 260 depicted in FIG. 2D. The flexibility of the pins 260 allows the sensor 252 to be moved relative to the lens assembly 251 to adjust magnification and relative to the circuit board 262 without damaging the pins 260.

One of ordinary skill in the art could appreciate that the relative distances and the magnification power mentioned in the embodiments described in FIGS. 2A, 2B, 2C, 2D, 2E and 2F are for illustration purposes only and do not limit the specification described here in any way. The relative distance between the sensor device and lens assembly can be controlled to achieve multiple levels of magnification power as per the system requirement.

FIG. 3 illustrates an endoscopy system comprising a magnification control system in accordance with an embodiment of the present specification. As shown in FIG. 3, the endoscopy system 300 comprises a first section 310 coupled to a second section 320 via a third section 330. In an embodiment, first section 310 corresponds to a distal tip of an endoscope, attached to a distal end of an insertion tube, which includes at least one objective lens assembly. The second section 320 corresponds to the control handle section of an endoscope device which includes the controls required to operate the device. In an embodiment, third section 330 is a magnification control system which is incorporated within the insertion tube portion connecting the distal end of the endoscope device with its control handle section.

First section 310, in an embodiment, comprises the imaging system, shown and described with respect to FIG. 1B, that includes a plurality of lenses 301 and a sensor device 302 adapted to capture the imaging information. In an embodiment, the sensor device 302 is a charge coupled device (CCD) or Complementary Metal Oxide Semiconductor (CMOS) or other similar kind of solid state device known in the art for capturing and storing image information received through the objective lens assembly 301. The sensor device 302 is coupled to the magnification control system 330.

In an embodiment of the present specification, the magnification control system 330 comprises a tube 305 having cylindrical portions 304a and 304b at each end. In alternate embodiments, the portions 304a and 304b can be configured in other shapes which can be adapted to contain liquid and/or gas. A first hub 303a is connected to cylindrical portion 304a while a second hub 303b is connected to cylindrical unit 304b. In an embodiment, the connection between hubs 303a and 303b and cylindrical portions 304a and 304b, respectively, is air tight. Thus, magnification control unit 330 is an air tight system, thereby allowing a change in pressure in one end of the tube 305 to be communicated to the other end of the tube. In an embodiment, tube 305 is manufactured using a flexible fiber or plastic material. In an embodiment, each of the hubs 303a and 303b comprise a piston.

In an embodiment, distal end 330a of the magnification control system 330, comprising the cylindrical unit 304a and hub 303a, is physically or electrically coupled to sensor device 302. Proximal end 330b of magnification control system 330, which comprises the cylindrical unit 304b and hub 303b is coupled to a control unit 306 through which a user can control the operation of magnification control unit 330. In an embodiment, the control unit 306 comprises the control section in the handle portion of a typical endoscope device, as described above, and also includes the control buttons required to operate the magnification control system 330.

One of ordinary skill in the art would appreciate that there could be multiple ways to couple the sensor device 302 with the hub 303a. In an embodiment of the present specification, the hub 303a is coupled to the sensor device 302 through a mechanical system such as a control wire. In another embodiment, the hub 303a is coupled to the sensor device 302 using an electrical control system. In an embodiment, the hub 303a is coupled to the sensor device 302 through a printed circuit board located on the back side of the sensor device 302.

In an embodiment, a user can control the magnification power of the endoscopy system 300 by changing the position of the sensor device 302 which is coupled to the magnification control unit 330 as described above. In an embodiment, on receiving an input from control unit 306, hub 303b, located on the proximal end 330b of the magnification control system 330, is pushed distally into the cylindrical unit 304b. As the magnification control unit 330 comprising the cylindrical units 304a, 304b and the tube 305 is an air tight system, movement in a distal direction (shown by arrow 311) of hub 303b exerts air pressure on the hub 303a located at the distal end 330a of the magnification control system 330, which is also pushed in the distal direction 311. The hub 303a is coupled to the sensor device 302 in a manner such that any movement in distal direction 311 of the hub 303a is translated in a corresponding movement in distal direction 311 of sensor device 302. The movement of the sensor device 302 closer to the objective lens assembly 301 leads to a decrease in the magnification power of the endoscope system 300. Conversely, any movement of hub 303b in a proximal direction (shown by arrow 312) would lead to movement of the sensor device 302 away from the objective lens assembly 301 and result in an increase in magnification.

In another embodiment, the hub 303a is coupled to distal cylindrical unit 304a such that any pushing movement of hub 303b in a distal direction 311 is translated to a pulling movement on hub 303a in a proximal direction 312 as explained with reference to FIG. 4 in subsequent sections of the present specification. Since hub 303a is coupled to the sensor device 302 such that movement of hub 303a results in movement of sensor device 302 in the same direction, in this embodiment, a pushing movement on hub 303b in a distal direction 311 leads to a pulling movement of the sensor device 302 in a proximal direction 312 away from the optical assembly 301 and results in an increase in magnification. Conversely, in this embodiment, any movement of hub 303b in a proximal direction 312 leads to movement of the sensor device 302 toward the objective lens assembly 301 and results in a decrease in magnification.

In an embodiment a processor in the control unit 306 generates a signal (in response to a user input) adapted to cause the hub 303b to move a predefined distance. The generated signal is communicated to a motor/actuator device (not shown in the figures) that is physically coupled to the hub 303b and causes the movement of the hub 303b Further, in an embodiment, the hub 303b is a planar structure vertically positioned within the tube 305 and covering the entirety of the tube area such that no air can pass from the volume positioned between the hubs 303b and 303a to an area beyond the hubs. The motor/actuator device causes the hubs 303b and 303a to move either proximally or distally depending on the signal received. In an embodiment, the hubs 303b and 303a are planar or curved structures that are sized to fit within, and completely encompass the internal area of, the tube 305, thereby creating an air tight fit. In one embodiment, the hubs are placed in a friction-fit relation to the tube, thereby permitting them to move upon application of a force.

In various embodiments, the hub 303b is moved relative to the cylindrical unit 304b by an incremental distance ranging from 0.01 mm to 0.2 mm over a total distance ranging from 0.01 mm to 1.0 mm and, correspondingly, the hub 303a is moved relative to the cylindrical unit 304a by an incremental distance ranging from 0.01 mm to 0.2 mm over a total distance ranging from 0.01 mm to 1.0 mm.

In embodiments, in a first position the sensor device is placed at a distance ranging from 0.07 mm to 1.7 mm from the lens assembly and when the sensor is moved away from the lens assembly to a second position, the distance of the second position from the lens assembly ranges from 1.8 mm to 2.7 mm.

In an embodiment with relatively lower dynamic magnification capability, the optical assembly is configured such that in an initial position the sensor device is placed at a distance of approximately 1.0 mm from the lens assembly and when the sensor device is moved away from the lens assembly it is moved to a maximum distance of 1.3 mm away from the lens assembly. The movement of sensor device from 1.0 mm distance to 1.3 mm distance can be in a single step or in incremental steps having a distance as low as 0.01 mm.

In an alternative embodiment with relatively higher dynamic magnification capability, the optical assembly is configured such that in an initial position the sensor device is placed at a distance of approximately 1.2 mm from the lens assembly and when the sensor device is moved away from the lens assembly it is moved to a maximum distance of 2.2 mm away from the lens assembly. The movement of sensor device from 1.2 mm distance to 2.2 mm distance can be in a single step or in incremental steps having a distance as low as 0.01 mm.

In an embodiment, the optical assembly is configured such that relative movement of sensor device by approximately 0.2 mm distance with respect to the position of the lens assembly leads to a change in magnification factor of approximately 2×. For example, in one embodiment, at a first 'default' view or magnification, the sensor is placed at a first position approximately 1.2 mm from the lens assembly. At a second, 'magnified' view or magnification, the sensor is moved to a second position which is approximately 1.4 mm from the lens assembly, or 0.2 mm further from the lens assembly than the first position. At said second distance of 1.4 mm, the magnification is increased by a factor of 2×. In various embodiments, the change in magnification power is not linear and is dependent upon the initial and final relative positions of the sensor device and objective lens assembly.

One of ordinary skill in the art would appreciate that there could be multiple methods of translating the user input received through control unit 306 into movement of the hub 303b to practice the present invention. In an embodiment, the user input is received through a control switch which is coupled to mechanical system such as a control wire connected to the hub 303b. As the user changes the position of control switch, the position of hub 303b, which is coupled to the control wire is accordingly changed. In another embodiment, the user input is received through a control button which is coupled to an electrical system such as a motor which enables the movement of hub 303b.

In an embodiment, the user can reverse the change in magnification level (i.e. increase or decrease the magnification level) of the image by providing corresponding input from control unit 306. On receiving user instruction to increase the magnification level, in one embodiment, pressure is exerted on the hub 303b to withdraw it from the cylindrical unit 304b in a proximal direction 312. With movement of hub 303b in a proximal direction 312, since the magnification control unit 330 is an air tight system, there is a pressure differential which exerts pressure on the hub 303a causing it to retract into cylindrical unit 304a. The sensor device 302 is coupled to hub 303a such that the proximal movement of the hub 303a pulls the sensor device away from the objective lens assembly 301, leading to a dynamic increase in the magnification level of image captured by the optical imaging system described here. As described above, in other embodiments, hub 303a can also be coupled to cylindrical portion 304a such that movement of hub 303b in a first direction is translated into movement of hub 303a in the opposite direction.

In an embodiment, the position of hub 303a and the corresponding sensor device 302 can be moved incrementally so that varying levels of resulting magnification power can be achieved. In another embodiment, the endoscope system 300 comprises only two levels of magnification power—regular magnification power and enhanced magnification power. Correspondingly, in such a system, the movement of the hubs 303a, 303b and the sensor device 302 is restricted between two positions.

FIG. 4 illustrates an endoscopy system comprising a magnification control system in accordance with another embodiment of the present specification. As shown in FIG. 4, the endoscope system 400 comprises a first section 410 and a second section 420 coupled via a third section 430. In an embodiment, the first section 410 corresponds to a portion of the tip section of an endoscope device which contains the objective lens assembly 401 and sensor 402. The second section 420 corresponds to the control handle section of an endoscope device which comprises a majority of the controls required to operate the device. The third section 430 comprises the magnification control system which, in an embodiment, is positioned within the insertion tube portion connecting the distal end of the endoscope device with its control handle section.

The first section 410 comprises the imaging system that includes an objective lens assembly 401 and a sensor device 402 adapted to capture the imaging information. In an embodiment of the present specification, the magnification control system 430 comprises a tube 405 having cylindrical portions 404a at a first, distal end and 404b at a second, proximal end.

A hub 403 is connected to cylindrical portion 404a. The distal end 430a of the magnification control system 430, which includes cylindrical unit 404a and hub 403, is coupled to the sensor device 402.

The proximal end 430b of the magnification control system 430, which includes cylindrical portion 404b, is connected to a control mechanism 411 that is used to control the magnification power of the system. In an embodiment, the control system 411 coupled to cylindrical portion 404b comprises a piston 406 which in turn is coupled to a control button 407 through a connector rod member 408. In an embodiment, a spring 409 is positioned over the connector rod member 408.

In an embodiment, the portion of the system comprising the tube 405 having cylindrical portions 404a at a first, distal end and 404b at a second, proximal end is a closed system that is filled with a fluid. In some embodiments, the fluid may be but is not limited to water or alcohol. To change the magnification power of the endoscope system 400, the user provides a corresponding input through the control button 407. In an embodiment, the user input may be purely mechanical in nature.

In an alternate embodiment, the user input may be provided using an electrical control system that translates into mechanical movement of the piston. The control button 407 converts the user input into a pressure, thereby moving piston 406 either towards the distal end 430a (distally) or towards the proximal end 430b (proximally). In one embodiment, hub 403 is coupled to cylindrical portion 404a in a manner such that movement of piston 406 in a first direction results in movement of hub 403 in a second direction opposite to said first direction. Therefore, if piston 406 is pushed distally into the cylindrical unit 404b, it exerts a pull pressure at the distal end 430a of the magnification control system 430, causing hub 403 to move in a proximal direction. The hub 403, located at the distal end 430a and coupled to cylindrical portion 404a, is coupled to the sensor device 402 in a manner such that any movement of the hub 403 is translated into a corresponding similar movement of sensor device 402. Thus, if piston 406 is pushed distally, the hub 403 and consequently the sensor device 402 is moved away from the objective lens assembly 401, leading to an increase in magnification power of the endoscope system 400.

Similarly, when the piston 406 is pulled proximally using control button 407, the hub 403 is at least partially extended distally from cylindrical unit 404a towards the objective lens assembly 401, leading to a similar change in position of the sensor device 402. The movement of sensor device 402 closer to the objective lens assembly 401 leads to a reduction in magnification power of the endoscopy system 400.

Figure 5A:
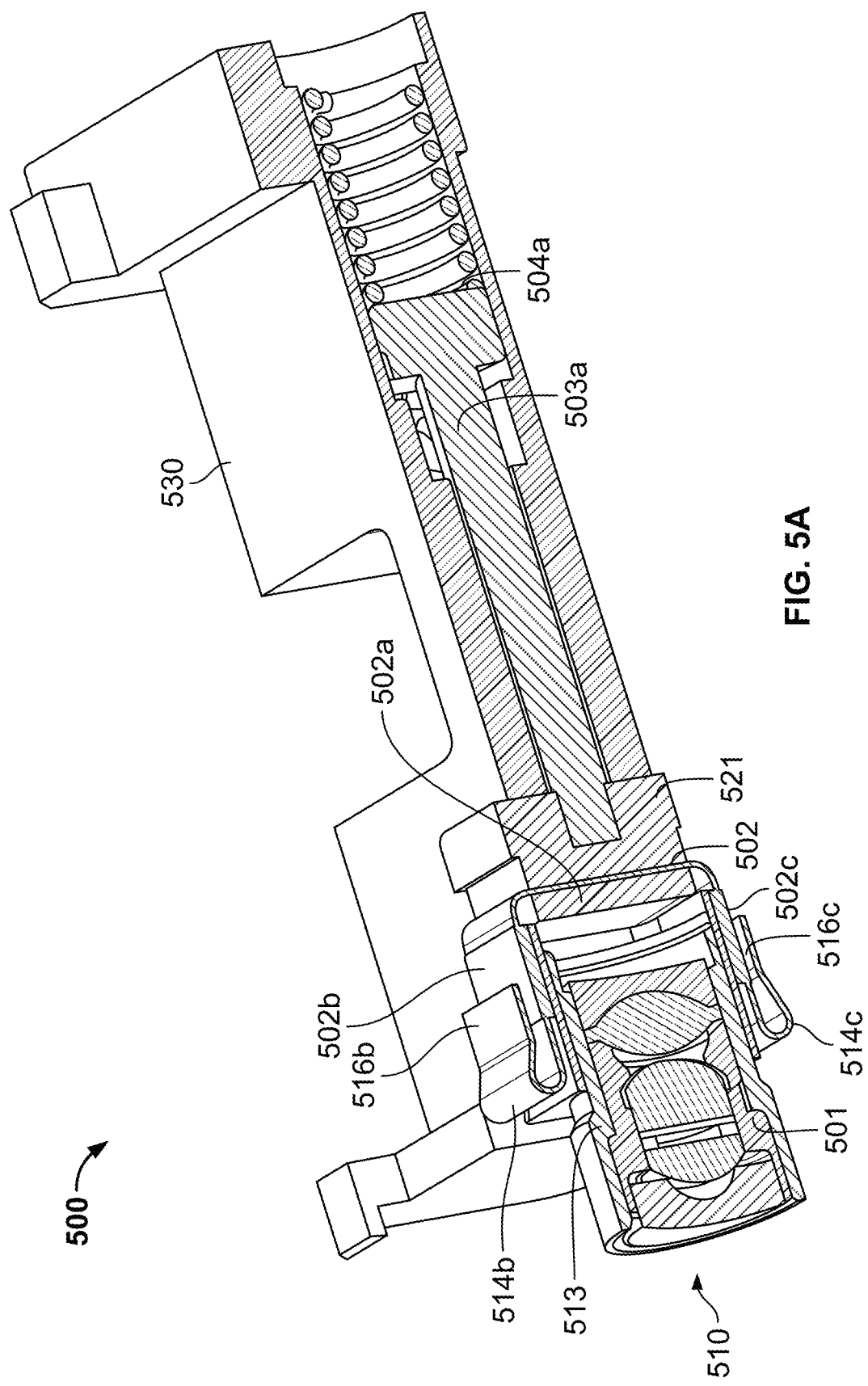
FIG. 5A illustrates cross-section of a side view of a distal end of an endoscopy system comprising a magnification control system, in accordance with an embodiment of the present specification.
Figure 5B:
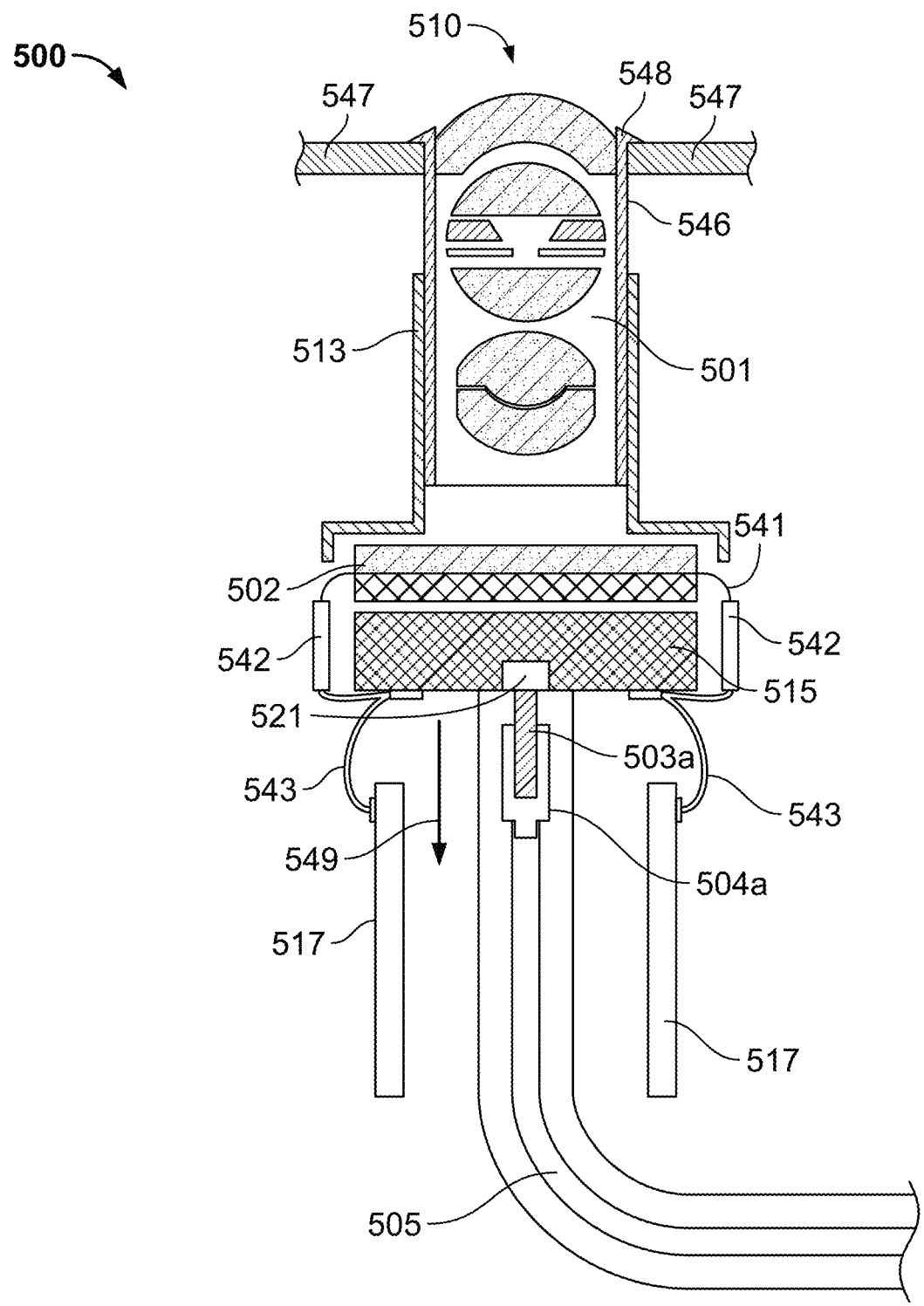
FIG. 5B illustrates cross-section of another side view of a distal end of an endoscopy system comprising a magnification control system, in accordance with an embodiment of the present specification.
Figure 5C:
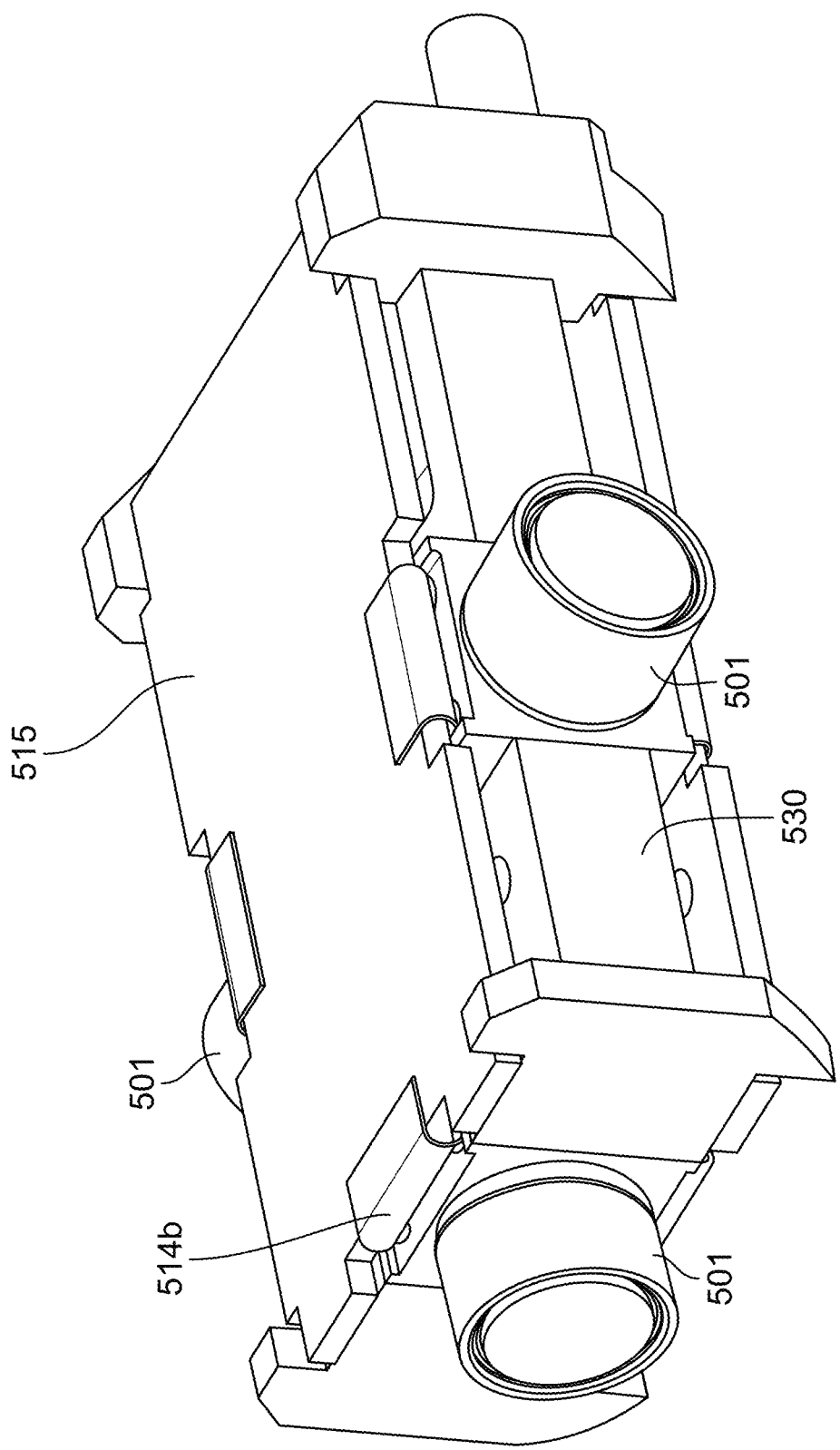
FIG. 5C illustrates a base board for coupling with the distal end of the endoscopy systems of FIGS. 5A and 5B.
Figure 5E:
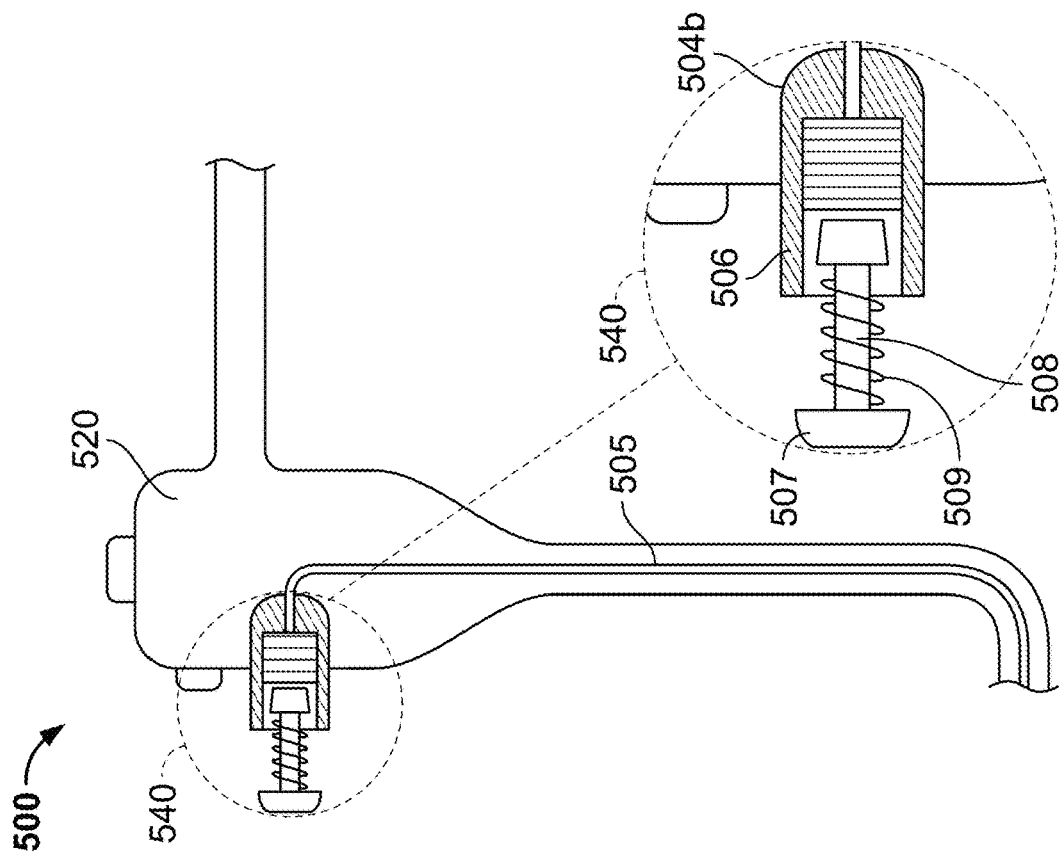
FIG. 5E illustrates a detailed plan view of a magnification control system located within a control handle portion of an endoscope, in accordance with an embodiment of the present specification.
Figure 5D:
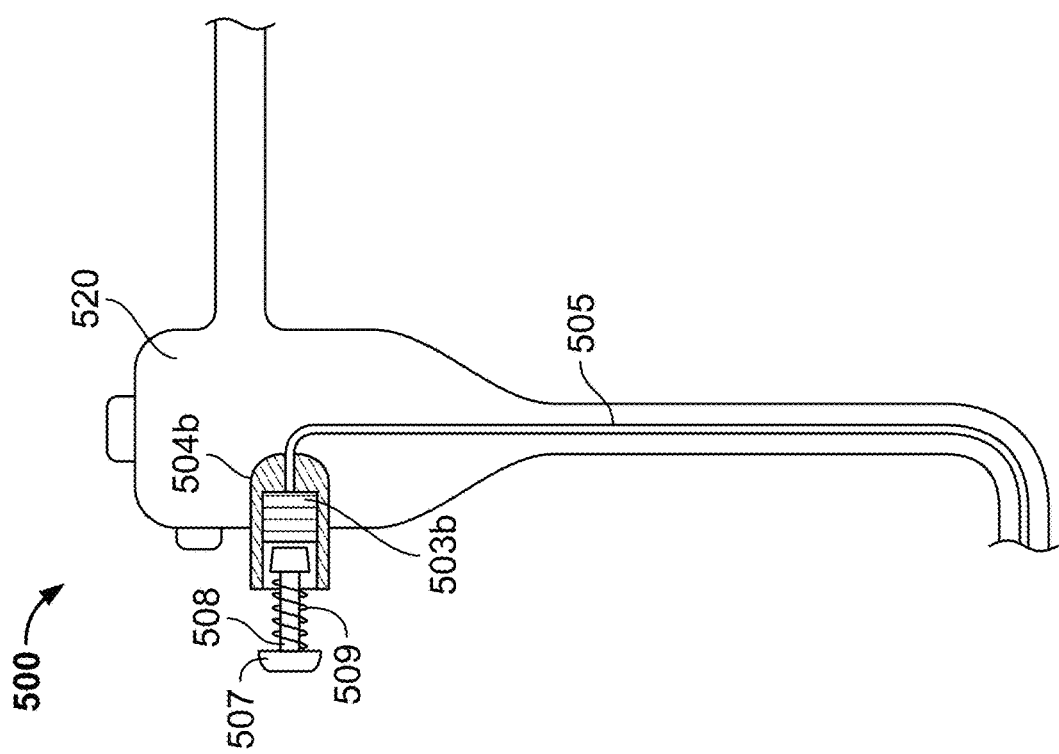
FIG. 5D illustrates a detailed plan view of a control handle portion of an endoscopy system comprising a magnification control system, in accordance with an embodiment of the present specification.

FIGS. 5A and 5B are side cross sectional views of a distal end of an endoscopy system 500 comprising a magnification control system and FIG. 5C is a top view illustrating a base board 515 adapted to support the viewing elements and sensors (thus, optical assemblies) and illuminators of the endoscopy system 500 of FIGS. 5A and 5B, in accordance with an embodiment of the present specification. FIG. 5D illustrates a control handle portion of an endoscopy system comprising a magnification control system, and FIG. 5E illustrates an enlarged view of the magnification control system, in accordance with some embodiments of the present specification. Referring to FIGS. 5A, 5B, 5C, 5D and 5E together, a distal end 510 of the endoscope system 500 comprises an optical assembly which comprises an objective lens assembly 501, a sensor device 502 and printed circuit boards 515. Metal frame 530 represents an outer portion which supports the entire optical assembly. Objective lens assembly 501 includes a plurality of objective lenses which are positioned inside a lens holder 513. One of ordinary skill in the art would appreciate that the above configuration resembles the basic camera assembly for an endoscope system comprising the objective lens and the sensor device and is well known in the art.

In an embodiment, referring to FIG. 5A, the sensor device 502 comprises a vertical portion 502a, a first horizontal portion 502b and a second horizontal portion 502c, wherein the first horizontal portion 502b and second horizontal portion 502c serve as image sensor contact areas. Each of the horizontal sections 502b and 502c comprise a distal end coupled with the vertical portion 502a and a proximal end coupled with folded over portions 514b and 514c respectively, which facilitate the movement of the sensor device 502, relative to lens assembly 501.

In an embodiment, the proximal ends of horizontal sections 502b, 502c are coupled with folded over portion 514b, 514c respectively in such a manner that the folded over portions are movable with respect to the horizontal sections. As described in an earlier embodiment with reference to FIGS. 2A-2C, each of the image sensor contact areas 502b and 502c comprise a connector strip on its proximal end for the movement of dynamic portions 514b, 514c which enable the movement of sensor device 502 along the axis of objective lens assembly. The dynamic portions 514b, 514c are configured such that they also couple the image sensor contact areas 502a and 502b to the circuit board 515 via connection portions 516b and 516c respectively.

In another embodiment, referring to FIG. 5B, the sensor 502 includes pins 542 which extend in a proximal direction from two opposing sides of the sensor 502. First flexible printed circuit board cables 541 connect the pins 542 to the sensor 502 at a distal end of said cables 541 and to a connection point 545 on a proximal surface 515p of a first printed circuit board 515 at a proximal end of said cables 541. Distal ends of second flexible printed circuit board cables 543 are connected to the proximal ends of the first flexible printed circuit board cables 541 at the connection point. Proximal ends of the second flexible printed cables 543 connect to second printed circuit boards 517. The first and second flexible printed circuit board cables 541, 543 allow movement of the sensor 502 relative to the objective lens assembly 501, which is fixed in an outer portion 547 of the endoscope by glue 548 between the barrel 546 of the objective lens assembly and said outer portion 547. Actuation of the magnification control system, through tube 505 and hub 503a, results in movement of the sensor in a proximal direction 549 away from the objective lens assembly 501, increasing magnification. Second flexible printed circuit board cables 543 are compressed as the sensor 502 moves in a proximal direction 549, and their flexibility allows them to move without breaking.

The present specification describes unique systems and methods for dynamically controlling the magnification power of a medical probe, such as an endoscope, as described in FIG. 3 and FIG. 4. In an embodiment of present specification, referring to FIGS. 5A through 5E, the sensor device 502 is coupled to a magnification control system 540 which comprises two cylindrical portions 504a and 504b connected at either end of a tube 505. In an embodiment, the cylindrical section 504a is coupled to a hub 503a and cylindrical section 504b is coupled to a hub 503b. In an embodiment, the hub 503a is coupled to the sensor 502 through an adapter 521. In an embodiment, the hubs 503a and 503b serve as air-tight stoppers, creating an air-tight magnification control system. In an embodiment, tube 505 is manufactured using a material such as fiber or plastic. In an embodiment, the control body or the handle section 520 comprises a magnification control system 540 which includes a button 507 coupled to the hub 503b through a connecting portion 508 and a spring 509. In an embodiment, a user input via button 507 is translated into a pressure that causes movement of hub 503b and consequently hub 503a, due to fluid pressure exerted via tube 505, as explained with respect to FIGS. 3 and 4.

In an embodiment, the user input may be purely mechanical in nature. In an alternate embodiment, the user input may be provided using an electrical control system that translates into mechanical movement of the piston. The movement of hub 503a in the either direction enables the movement of the sensor 502 in the same direction such that any such change in the relative position of sensor 502 with respect to the position of objective lens assembly 501 leads to a change in the magnification power of endoscope system 500. In an alternate embodiment, the magnification control system 540 is configured such that the movement of hub 503a in either direction enables the movement of sensor 502 in an opposite direction as described in the embodiments in FIG. 3 and FIG. 4.

In the specific configuration shown in the embodiment of FIG. 5A, the sensor device 502 is coupled to a printed circuit board (PCB) 515, through dynamic portions 514b, 514c which are connected to the printed circuit board through connection portions 516b, 516c. One can appreciate that the dynamic portions 514b, 514c correspond to the dynamic portions 203b and 203c shown in FIGS. 2A through 2C. In an embodiment, PCB 515 comprises the electronics to control various functionalities in the endoscope system 500.

FIG. 5E is a detailed plan view of a configuration of a magnification control system 540 located within a handle portion 520 of an endoscope for implementing dynamic magnification control in accordance with an embodiment of the present specification as also shown in FIG. 4. As shown in FIG. 5E, the control body or handle section 520 of the endoscope system 500 comprises a magnification control system 540 which is coupled to the tube 505 as also illustrated in FIGS. 5A, 5B and 5D. In an embodiment, as shown in an expanded view, the magnification control system 540 comprises a control button 507 coupled to a piston 506 through connecting rod 508 surrounded by a spring 509. In an embodiment, the button 507 comprises markings (not shown in figure) indicating incremental movement of the sensor device 502 as explained in description of FIG. 3, 4, 5A and 5B corresponding to movement/turning of button 507. The markings help a user to move the sensor to a desired distance away from the lens assembly (being guided by the predefined increments marked on the button). In another embodiment, markings corresponding to incremental movement of the sensor may be provided on the handle 520, proximate to the button 507, such that movement of the button 507 may be guided by said markings to move the sensor by a desired distance.

The piston 506 is enclosed in a cylindrical body 504b which, in turn, is connected to the cylindrical section 504a shown in FIG. 5A through tube 505. In an embodiment, the space between the two cylindrical units 504a, 504b and the tube 505 is filled with a fluid such as water, oil, alcohol or air. Any pressure exerted through the piston 506 translates in movement of fluid or air within the closed system which in turn exerts pressure on the hub 503*a* leading to movement of the sensor device 502 as explained in description of FIG. 3, 4, 5A and 5B. Movement of sensor device 502 relative to the position of objective lens assembly 501 provides dynamic control over the magnification power of the endoscope system 500.

Figure 6:
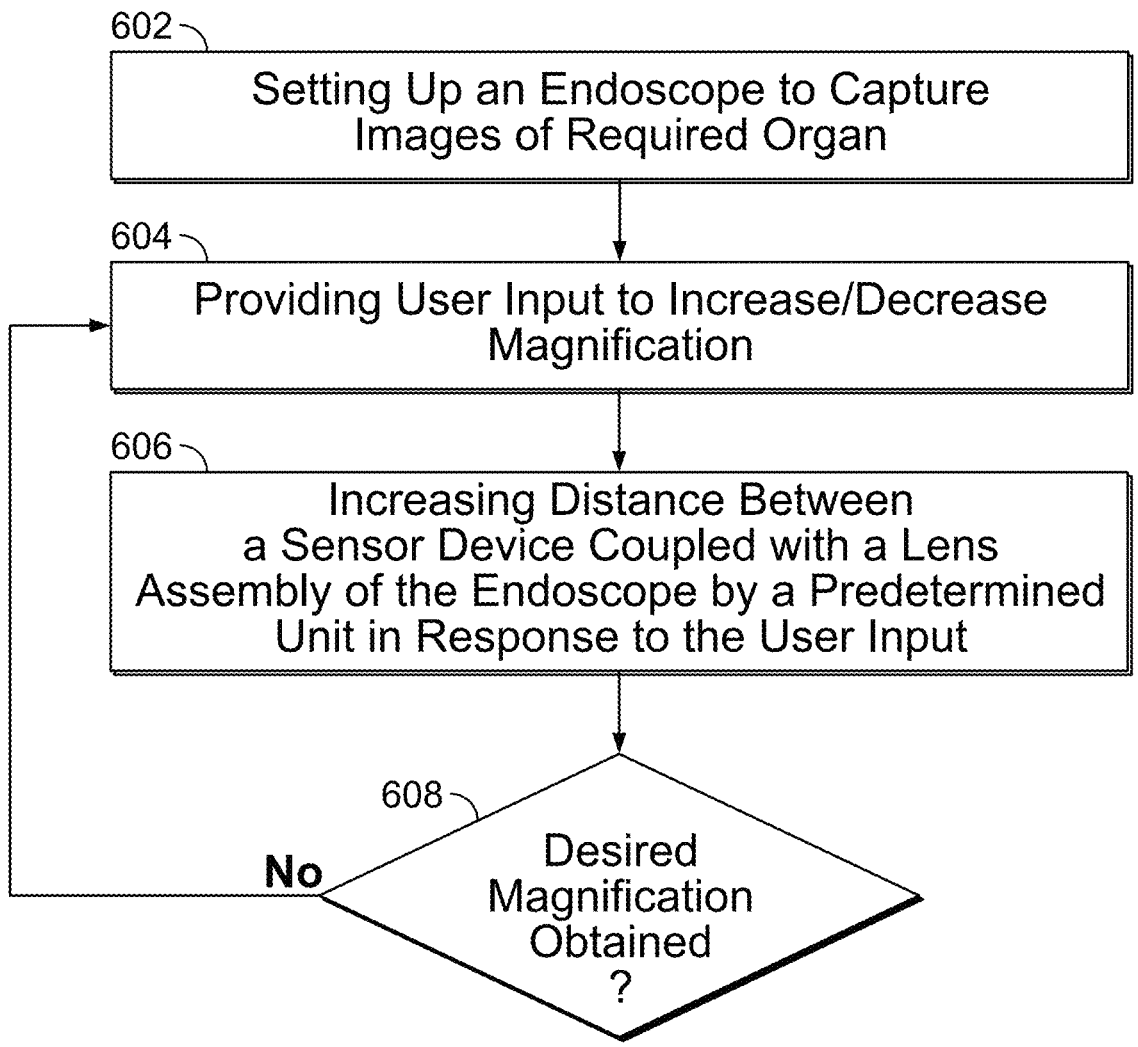
FIG. 6 is a flowchart illustrating a method of using an endoscope device comprising a magnification control system, in accordance with an embodiment of the present specification.

FIG. 6 is a flowchart illustrating a method of using an endoscope device comprising a magnification control system, in accordance with an embodiment of the present specification. The magnification control system is coupled to an image sensor for controlling the position of the image sensor relative to an objective lens assembly of the endoscope based on the level of image magnification (or zoom) required by a user. At step 602, the endoscope is used to capture images of required organ. A tip portion of the endoscope comprising the objective lens assembly, image sensor coupled with the magnification control system is inserted within a patient's body to obtain images of organs within. The tip section is controlled by a control system provided in a handle portion of the endoscope, which is connected to the tip section via an umbilical tube, as explained with reference to FIG. 1A. The control system also comprises the magnification control system to which a user input may be provided via a control located on the handle portion of the endoscope, as explained with reference to FIG. 1B.

At step 604, a user input is provided to increase magnification or zoom in on an image captured by the optical lens assembly. In an embodiment, the user input may be provided through a control switch (such as button 507 shown in FIGS. 5D and 5E), which is coupled to mechanical system such as a control wire connected to the magnification control system causing an increase or decrease in a distance between the objective lens assembly and the image sensor. In another embodiment, the user input is received through a control button which is coupled to an electrical system such as a motor which enables the movement of at least a portion of the magnification control system, thereby leading to movement of the image sensor towards or away from the objective lens assembly.

At step 606, a distance between the image sensor coupled with the lens assembly of the endoscope is increased or decreased by a predetermined unit in response to the user input. The mechanics enabling movement of the image sensor towards or away from the objective lens assembly have been explained in the preceding sections with reference to FIGS. 3, 4, and 5A-5E. As explained earlier, increasing the distance between the image sensor and the objective lens assembly leads to an increase (zoom in) in the magnification of the image captured and decreasing the distance between the image sensor and the objective lens assembly leads to a decrease (zoom out) in the magnification of the image captured.

At step 608 it is determined if the magnification achieved is sufficient. If further zooming in or out is desired, steps 604 and 606 are repeated until desired magnification is obtained.

The above examples are merely illustrative of the many applications of the system of present specification. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

In the description and claims of the application, each of the words "comprise" "include" and "have", and forms thereof, are not necessarily limited to members in a list with which the words may be associated.

We claim:
1. An endoscope comprising:
a proximal end comprising a control portion;
a distal end comprising a distal tip, wherein said distal tip comprises:
a lens holder,
a lens received by the lens holder,
a sensor device comprising:
a vertical portion,
a horizontal portion, and
a first component of a movable coupling, wherein the first component is coupled to the horizontal portion, and
a second component of the movable coupling, wherein the second component has a fixed position relative to the lens, wherein the first and the second components are movably coupled to each other and configured to move proximally and distally relative to each other, upon actuation of the control portion, to adjust a distance between the vertical portion and the lens.

2. The endoscope of claim 1, wherein the vertical portion includes an image sensor.

3. The endoscope of claim 1, wherein:
the horizontal portion is a first horizontal portion,
the sensor device further includes second horizontal portion, and
the first and second horizontal portions are on opposite sides of the lens holder.

4. The endoscope of claim 1, wherein the first component receives the second component.

5. The endoscope of claim 1, wherein the second component includes a pair of proximal walls connected by a distal curved wall.

6. The endoscope of claim 1, wherein the distal end further comprises a housing, and wherein the lens holder, the lens, and the second component are positionally fixed relative to the housing.

7. The endoscope of claim 6, wherein the sensor device is movable relative to the housing.

8. An endoscope comprising:
a proximal end comprising a control portion;
a distal end comprising a distal tip, wherein said distal tip comprises:
a lens holder,
a lens received by the lens holder,
a sensor device comprising:
a vertical portion,
a horizontal portion, and
a first component of a movable coupling, wherein the first component is coupled to the horizontal portion,
a printed circuit board coupled to the vertical portion by a flexible coupling, and
a second component of the movable coupling, wherein the second component has a fixed position relative to the lens, wherein the first and the second components are movably coupled to each other and configured to move proximally and distally relative to each other, upon actuation of the control portion, to adjust a distance between the vertical portion and the lens, and between the vertical portion and the printed circuit board.

9. The endoscope of claim 8, wherein the vertical portion includes an image sensor.

10. The endoscope of claim 8, wherein:
the horizontal portion is a first horizontal portion,
the sensor device further includes second horizontal portion, and
the first and second horizontal portions are at opposite sides of the lens holder.

11. The endoscope of claim 8, wherein the first component receives the second component.

12. The endoscope of claim 8, wherein the second component includes a pair of proximal walls connected by a distal curved wall.

13. The endoscope of claim 8, wherein the distal end further comprises a housing, and wherein the lens holder, the lens, and the second component are positionally fixed relative to the housing.

14. The endoscope of claim 13, wherein the sensor device is movable relative to the housing.

* * * * *